(12) United States Patent
Torrie et al.

(10) Patent No.: US 11,969,166 B2
(45) Date of Patent: Apr. 30, 2024

(54) HIP CAPSULE CLOSURE

(71) Applicants: Smith & Nephew, Inc., Memphis, TN (US); Smith & Nephew Orthopaedics AG, Zug (CH); Smith & Nephew Asia Pacific Pte Limited, Singapore (SG)

(72) Inventors: Paul Alexander Torrie, Marblehead, MA (US); Jessica Marie Grabinsky, Melrose, MA (US); Marc Joseph Balboa, Hopkinton, MA (US); Benjamin Michael Hall, Roslindale, MA (US); Timothy Young, Natick, MA (US)

(73) Assignees: Smith & Nephew, Inc., Memphis, TN (US); Smith & Nephew Orthopaedics AG; Smith & Nephew Asia Pacific Pte. Limited

( * ) Notice: Subject to any disclaimer, the term of this patent is extended or adjusted under 35 U.S.C. 154(b) by 174 days.

(21) Appl. No.: 17/496,228

(22) Filed: Oct. 7, 2021

(65) Prior Publication Data

US 2022/0104804 A1 Apr. 7, 2022

Related U.S. Application Data

(60) Provisional application No. 63/088,595, filed on Oct. 7, 2020.

(51) Int. Cl.
*A61B 17/04* (2006.01)

(52) U.S. Cl.
CPC .. *A61B 17/0491* (2013.01); *A61B 2017/0496* (2013.01)

(58) Field of Classification Search
CPC ............ A61B 17/0491; A61B 17/0469; A61B 2017/0409; A61B 17/0483; A61B 2017/0488; A61B 2017/0417; A61B 17/3403; A61B 17/0482; A61B 17/0625; A61B 17/062; A61B 2017/00349; A61B 2017/00663
See application file for complete search history.

(56) References Cited

U.S. PATENT DOCUMENTS 7,153,312 B1 * 12/2006 Torrie ................ A61B 17/0401
606/144
2002/0107531 A1 * 8/2002 Schreck ............... A61B 17/064
606/142

(Continued)

*Primary Examiner* — Erich G Herbermann
*Assistant Examiner* — Aman Kumar Mann
(74) *Attorney, Agent, or Firm* — Norman F. Hainer, Jr.; Kate Ryland Tetzlaff

(57) ABSTRACT

Systems and methods of repairing tissue are disclosed. Systems and methods may repair an opening through a hip capsule. Systems and methods preferably repair the tissue while minimally encroaching on the tissue immediately behind the repair, such as the hip joint tissues. Some systems may repair the tissue with a suture passer having a needle that slides in axial alignment with the passer and includes a first recess for passing the suture in a first axial direction and a second recess for passing the suture in an opposing axial direction. Some systems may pass a portion of a repair construct in a retrograde direction, placing the repair construct in a preferred arrangement accommodating for the stresses on the tissue.

19 Claims, 36 Drawing Sheets

(56) References Cited

U.S. PATENT DOCUMENTS

| | | | |
|---|---|---|---|
| 2003/0171764 A1* | 9/2003 | Debbas | A61B 17/0057 606/222 |
| 2007/0010857 A1* | 1/2007 | Sugimoto | A61B 17/00234 606/232 |
| 2007/0073319 A1* | 3/2007 | Mikkaichi | A61B 17/0487 606/153 |
| 2009/0177031 A1* | 7/2009 | Surti | A61B 1/00087 606/139 |

* cited by examiner

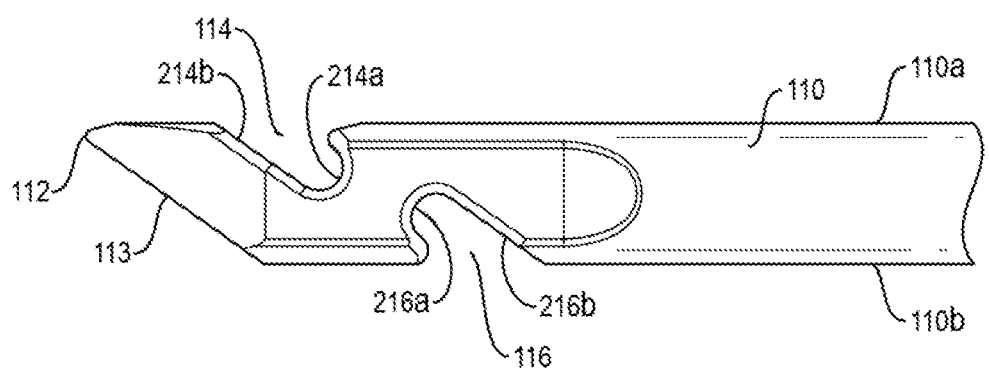
FIG. 7A
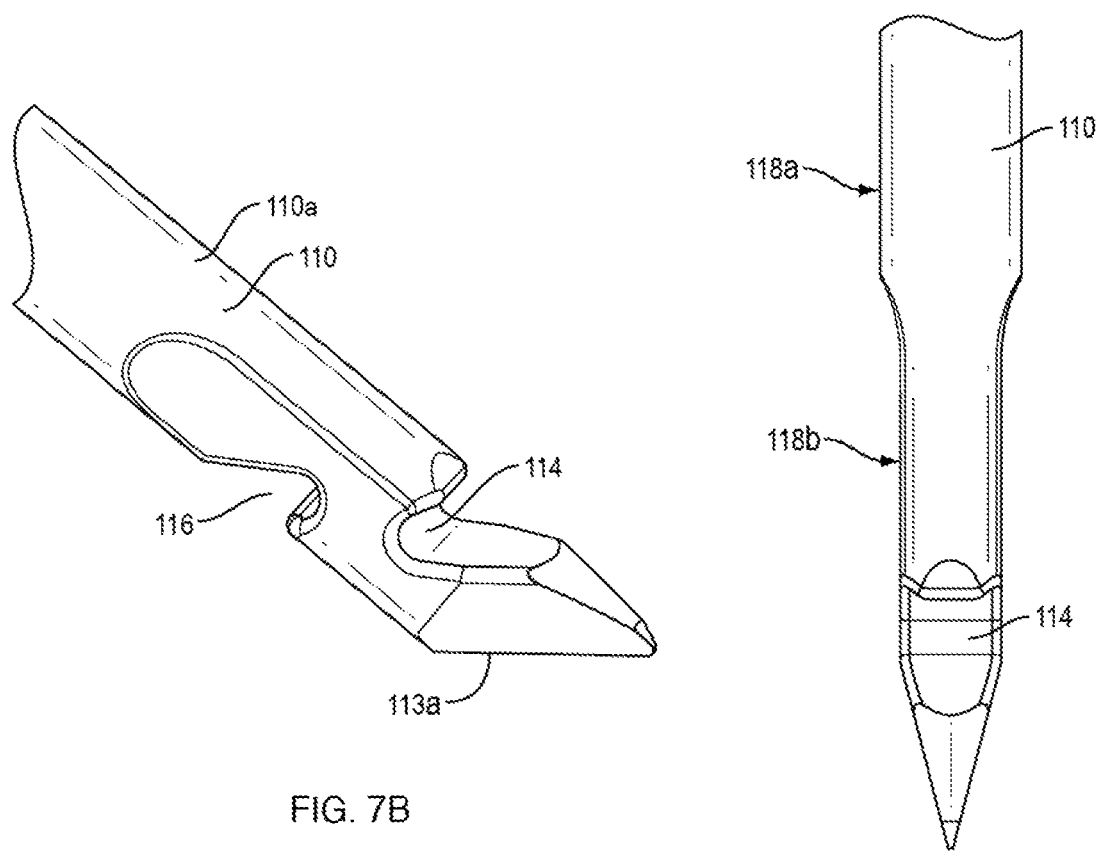
FIG. 7B
FIG. 7C
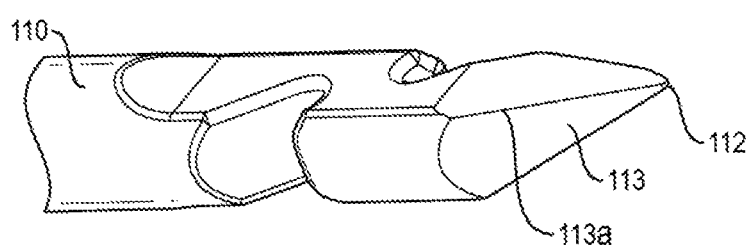
FIG. 7D

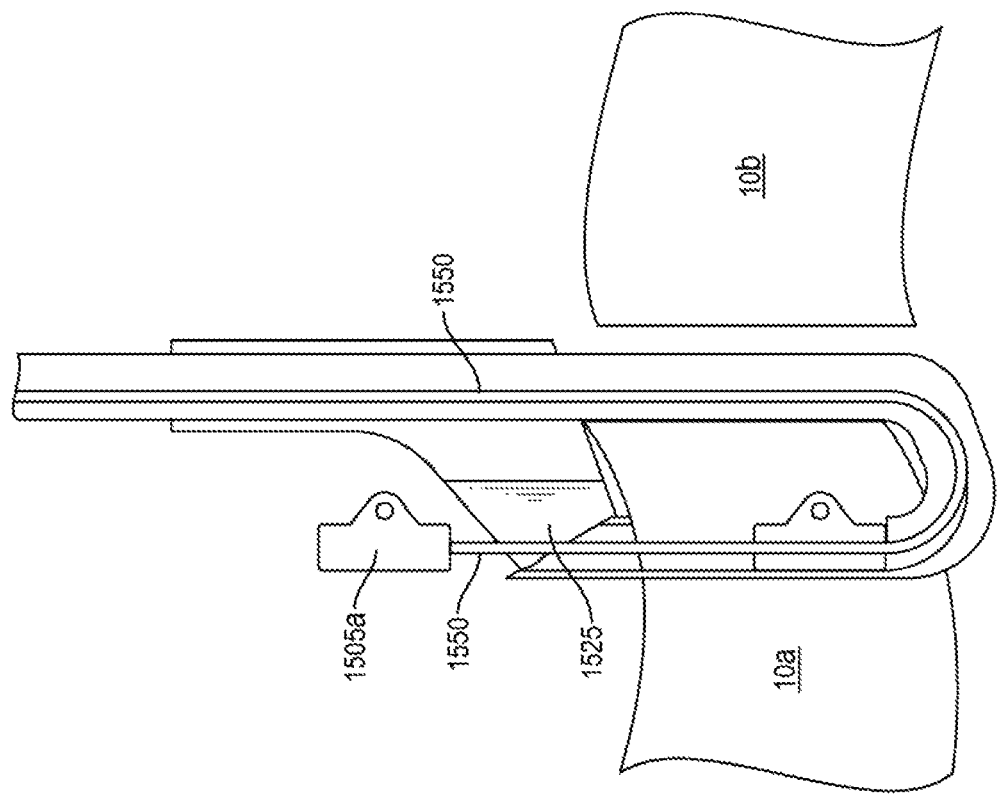
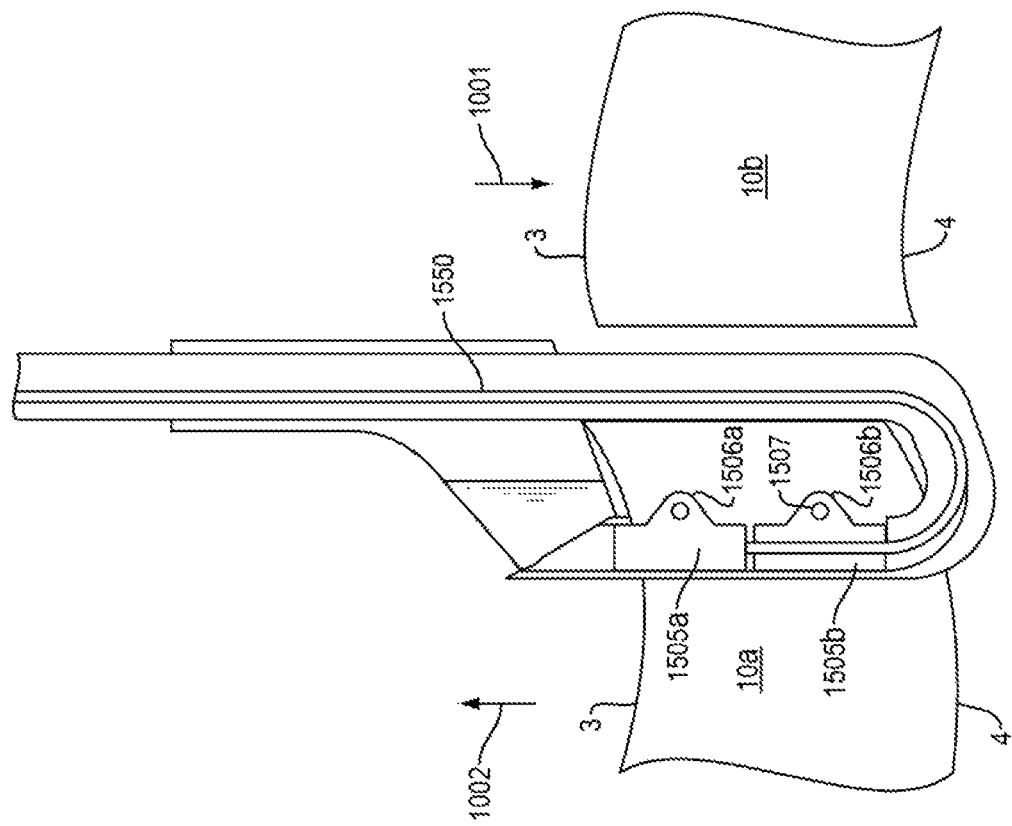

HIP CAPSULE CLOSURE

CROSS-REFERENCE TO RELATED APPLICATIONS

This application claims benefit to and incorporates by reference in its entirety, U.S. Provisional Pat. No. 63/088,595, filed Oct. 7, 2020; titled "HIP CAPSULE CLOSURE".

FIELD

The present invention relates to a surgical system that can pass a suture through sides of a tissue opening and repair the opening.

BACKGROUND

Arthroscopic surgery involves the performance of surgical procedures through small openings and under visualization using an arthroscope. Access to a target tissue is normally provided through one or more portals formed directly in the patient's body or through one or more cannulas inserted into the patient's body through small incisions. A desired surgical procedure is carried out by a surgeon with elongated small diameter instruments inserted through these cannulas.

Often it is necessary to pass a flexible member, such as suture or suture tape through tissue during these procedures. This may mend a tear or close an opening in the tissue for example. Although this task is not uncommon, passing and retrieving suture through tissue can be challenging in an endoscopic or arthroscopic procedure where visualization and space is limited. In addition, closing a tear or opening can require several passes and loops along the tear, adding to the challenge.

Various instruments have been developed to pass and retrieve suture through tissue during arthroscopic surgery for tissue repair. When closing a tissue opening, the suture may be threaded through two sides of a tissue, the tissue(s) drawn to the target location relative to each other and then fixed in place. For example, during hip procedures, the hip capsule that may have been opened for access to the target anatomy, requires closure. In this example, the ligaments around the hip are under some of the highest stress ligaments in the body, and therefore the ligaments and adjacent capsule tissue require high strength repairs. Therefore, any device, system or method must route the suture or equivalent flexible strand to form a strong repair. A strong repair preferably includes apposition of the tissue across the entire thickness of the capsule wall both acutely and as the capsule heals under the normal stresses on the capsule. A closure configuration therefore needs to ensure that proper compressive forces are maintained between the two sides of the capsule opening, often termed capsule leaflets. Preferably this is achieved with reduced procedural efforts and time to close the capsule.

FIG. 1 illustrates hip capsule tissue 10 with a tear or opening 20 that requires closing. Within or immediately behind the capsule tissue 10 is the joint tissue including the femoral head, cartilage, and the acetabular rim, collectively labeled 12. Access to the capsule tissue 10 through the joint tissue 12 is therefore limited and instrumentation is thereby limited to access preferably from the external side. Therefore, there is a need for a system that repairs the hip capsule opening 20, without encroaching (extending into or through) the joint tissue 12. This is problematic for typical instruments known in the art that repair tissue, as they may pass a suture (or equivalent) through two portions of tissue and fix the repair approaching the tissue from a first side of the tissue, placing a fixation device through and on the opposing side of the tissue. Following with this example and given the restriction to access via the joint tissue 12, these devices may approach the hip capsule from the external surface. It follows that these devices would therefore place fixation devices with the inner wall 4 of the capsule 10 within the joint capsule, as illustrated in FIG. 2A. In the case of the hip capsule however, fixation devices on the inner surface 4 may not be preferable. Whether fixation devices, are bundles or knots of suture, such as all-suture anchors, or more rigid key or button style anchors, they may both irritate or intrude on the joint during articulation, damaging tissue and inhibiting joint mobility. Secondly, fixation devices 5 in this location may not form a functional repair, given the stresses on the capsule tissue during use. FIG. 2A illustrates a repair with a suture 8 and fixation devices 5 on the interior wall 4 of capsule 10. This solution may asymmetrically close the tear, due to normal stresses on the capsule 10, thereby opening the repair at the inner surface 4, indicated by the arrows 25 in FIG. 2B, and form an incomplete repair across the full thickness of the capsule wall. Therefore, there is a need for a system that reliably closes a tear or opening in a tissue and maintains adequate compressive forces between the two sides of the opening 20 after closure, accommodating for the stresses on the tissue. There is a need for a system that reliable closes a tear of an opening in a tissue avoiding the joint 12.

SUMMARY

Described herein is an improved device and method for placing a suture or equivalent, through tissue to repair an opening therethough. Repairing may include abutting two sides of the opening and fixing it in that position. Devices and methods may pass a suture through two portions of tissue without removing the device to reload the suture. Described herein is an improved system and method of fixing a repair that places fixation devices on an external surface of repair.

A first example embodiment may include a suture passer with a handle, an elongate shaft extending distally therefrom, defining a passer longitudinal axis, and a jaw at a shaft distal end. The jaw distal end is in axial alignment with the passer longitudinal axis. The jaw distal end includes a cleat configured to selectively capture and release a suture. The passer includes a needle that slides in axial alignment with the passer longitudinal axis. The needle may have a first recess and a second recess axially spaced from each other along the needle. The first recess may retain and advance the suture distally across an axial opening of the jaw and into the cleat. The second recess may engage the suture while captured within the cleat and remove the suture therefrom.

In some particular embodiments, the first and second recess are on opposing sides of the needle. The needle may include a distal pointed tip for piercing tissue, disposed within the jaw. The needle may include a distal facing ramp extending proximally the distal pointed tip, the distal facing ramp defining a sliding surface with blunted edges. The distal facing ramp may engage a bridge portion of the suture and deflect the needle over the bridge portion. The bridge portion is disposed between bilateral sides of the cleat. The needle's ramped distal surface may engage the suture captured within the cleat and deflect the needle over the suture to place the suture within the second recess. The passer may include an axially sliding rod configured to slide between a recessed configuration and advanced configuration and in the advanced configuration it may engage the suture when captured within the cleat. Rod may supplement retention of the suture within the cleat. The rod may also interact with the needle ramped surface to deflect the needle as the needle advances to engage the suture while captured within the cleat.

A method of passing a suture with a suture passer sequentially through two sides of an opening through a tissue is also disclosed. The method includes placing the suture passer within the opening between the two sides and passing a suture engaged with a first recess of a needle through a first of the two sides of the opening, the passing in a first axial direction. The method also includes passing the suture while engaged with a second recess of the needle through a second of the two sides of the opening, the passing in a second direction that is opposite to the first axial direction.

In some particular methods, the suture is placed within bilateral arms of a cleat to hold the suture after passing the suture through the first of the two sides of the opening. The method may also include axially advancing and deflecting the needle over a bridge portion of the suture held between the bilateral arms of the cleat to engage the bridge portion with the second recess before passing the length of suture in the second direction. Passing the suture while engaged with the first recess may include pushing the suture distally and passing the suture while engaged with the second recess may include pulling the length of suture proximally. The suture passer may remain between the two sides passing the suture through the first and second side. The suture passer extends from the tissue in a direction away from an internal joint immediately below the tissue while passing the suture through the two sides of tissue. Before passing the suture while engaged with a second recess of the needle, a suture bridge at a distal end of the passer may be captured within the second recess. This may include first engaging a ramped distal facing surface of the needle with the suture bridge and then continuing to axially advance the needle to slide the ramped distal facing surface over the bridge portion and deflect the needle over the bridge portion and then axially advancing the needle until the second recess is axially adjacent the bridge portion and thereby capturing the suture bridge within the second recess.

Another method of repairing an opening through tissue is disclosed, the opening disposed between a first leaflet and a second leaflet of a hip capsule. The method includes placing a distal end of a repair system along an internal surface of the first leaflet of tissue, a handle of the repair system extending from an external side of the tissue, on the other side of the hip capsule directly adjacent the first and second leaflets. The handle and shaft thereby avoid the hip joint. Repair system includes a repair construct and repair instrument. Using the repair instrument, a first fixation member and suture of the repair construct is passed in a retrograde direction towards the handle, from the internal surface to an external surface of the first leaflet. The suture of the repair construct is then extended through the second leaflet of tissue. A second fixation member of the repair construct is then placed on an external surface of the second leaflet of tissue. The suture is then tensioned to repair the opening through the tissue.

In some particular methods, tensioning the suture deploys at least one of the fixation members. Placing the second fixation member may comprise placing a distal end of the repair instrument along an internal surface of the second leaflet of tissue and passing the second fixation member in a retrograde direction through the second leaflet. Tensioning the suture may lock the opening in a repaired configuration. A proximal jaw of the repair instrument may be placed onto the external surface before passing the first fixation member. The fixation member or members may be passed, retrograde, though an opening through the proximal jaw. A piercing tip of the repair instrument may be passed through the first leaflet, in a retrograde direction before passing the first fixation member.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIG. 7A illustrates a side view of the needle, in accordance with this disclosure;

FIG. 7B illustrates a perspective view of the needle, in accordance with this disclosure;

FIG. 7C illustrates a top view of the needle, in accordance with this disclosure;

FIG. 7D illustrates a view of the needle illustrating the ramped end surface, in accordance with this disclosure;

FIGS. 15A-15H illustrate various views and methods of use of a repair system, in accordance with this disclosure.

DETAILED DESCRIPTION

Figure 1:
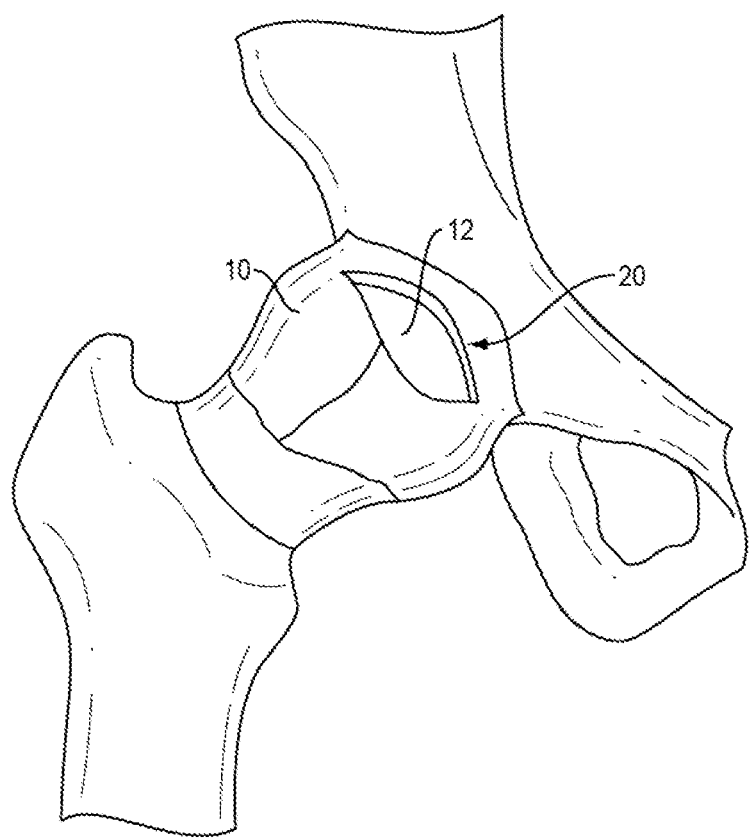
FIG. 1 illustrates a hip capsule opening, for reference purposes throughout the disclosure.
Figure 2A:
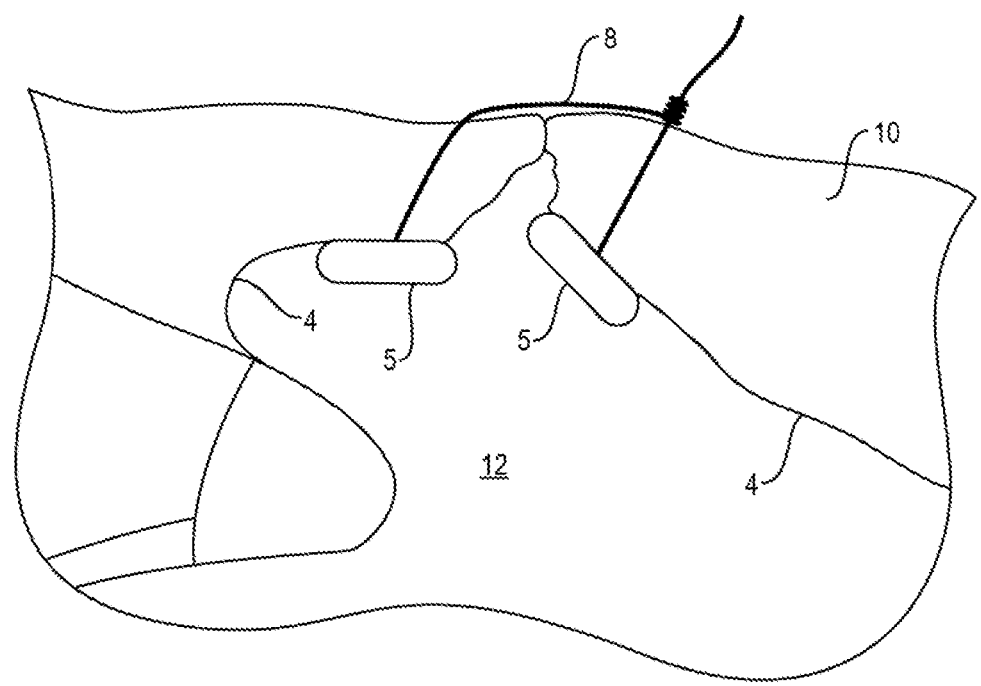
FIG. 2A illustrates a closure repair with fixation devices on an internal surface of the hip capsule.
Figure 2B:
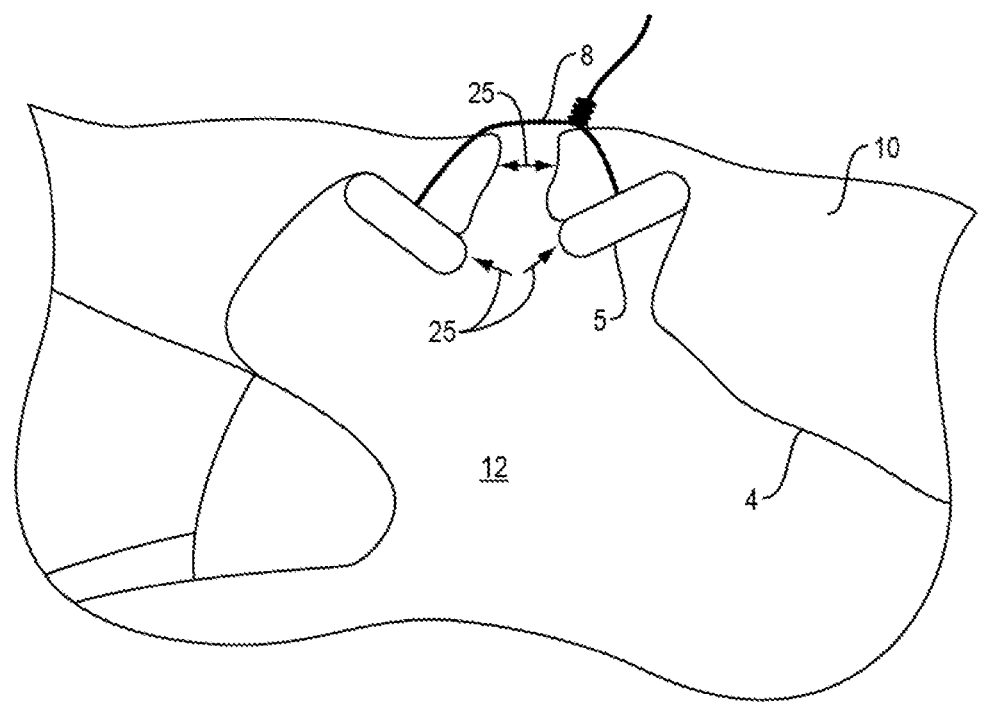
FIG. 2B illustrates a resulting repair configuration under load.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

This disclosure includes systems and method for forming an improved repair of an opening in tissue. These systems may close an opening through hip capsule tissue, such that the repair maintains adequate compressive forces between the capsule leaflets after closure, accommodating for the stresses on the tissue. The system places a repair construct through the capsule tissue while remaining substantially external to the hip joint and therefore not encroaching into the joint.

Figure 3:
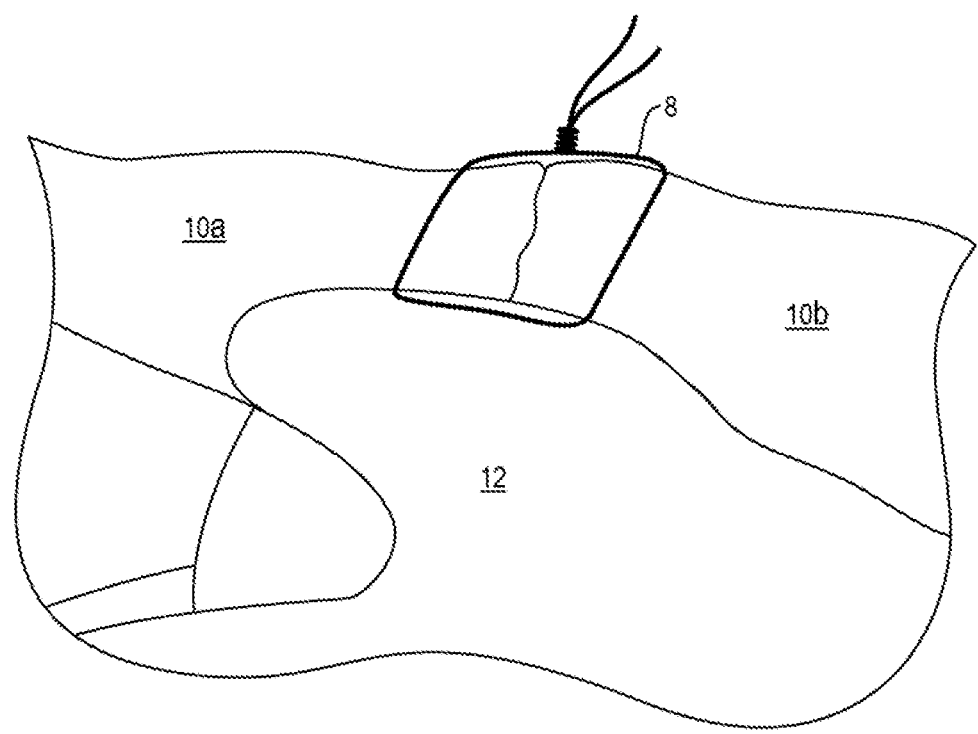
FIG. 3 illustrates a closure repair with a complete loop.
Figure 5:
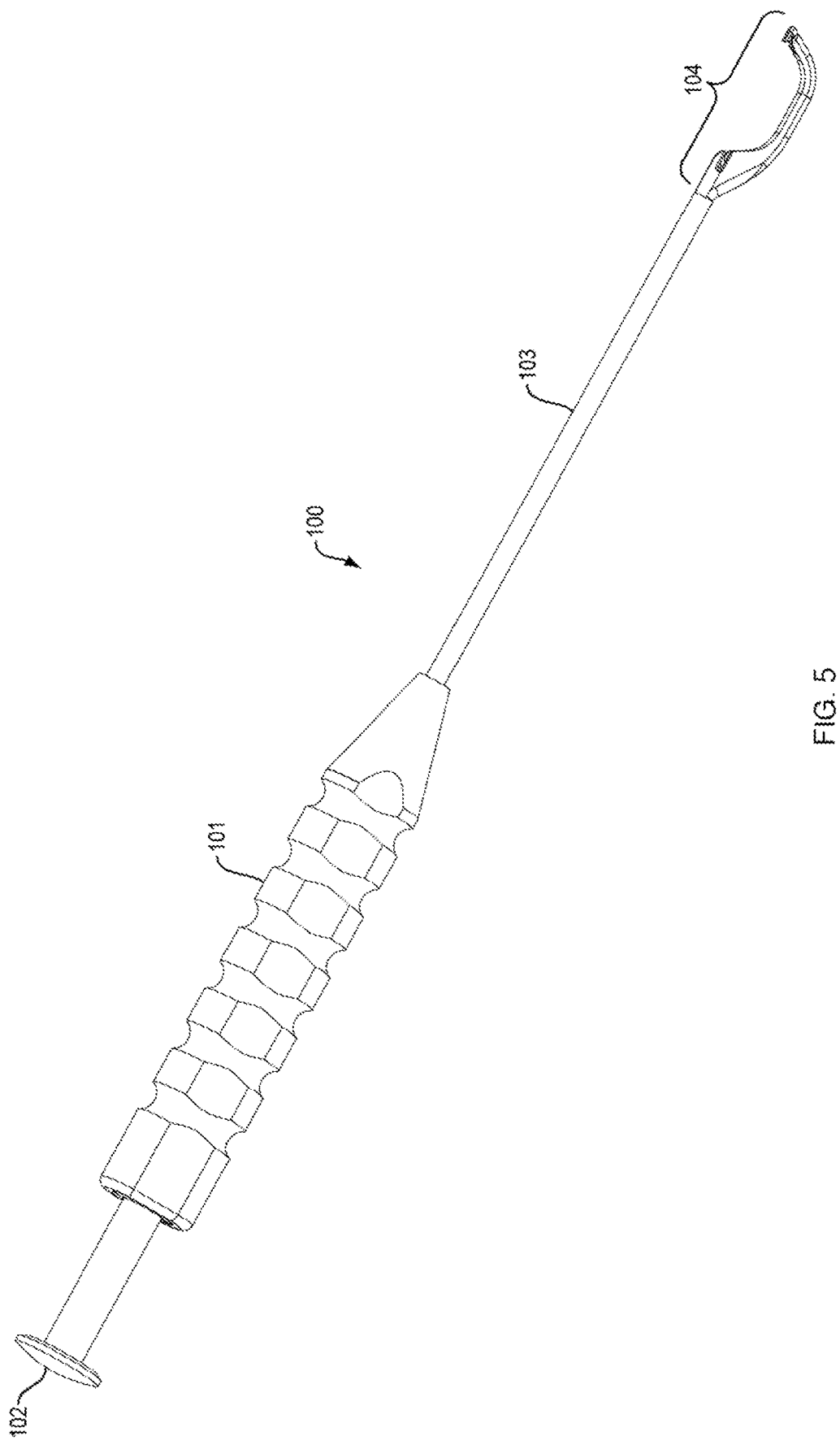
FIG. 5 illustrates a suture passer, in accordance with this disclosure.

Illustrated in FIG. 5 is a suture passer 100 in accordance with this disclosure, for passing a suture through at least two portions of tissue, such as for example two sides of an opening through a tissue. The two sides of an opening through the hip capsule are oftentimes called leaflets, 10a, 10b. Suture passer 100 may be used to place a suture through the two leaflets 10a, 10b, either side of hip capsule opening 20, while remaining substantially external to the hip joint 12. Passer 100 may preferably place suture through and around an opening through both leaflets without needing to be removed from the target site to reload the suture 8. Suture passer 100 may place a suture or equivalent in a continuous loop around the repair, as illustrated in FIG. 3. Suture 8 may be a braided flexible material, as known in the art. The term suture in the context of this disclosure encompasses flexible members such as but not limited to suture, suture tape, cable, ribbon, or wire. Passer 100 comprises a handle 101, a needle actuator 102 such as a lever, slide or button operatively coupled to the handle 101, an elongate shaft 103 extending distally from the handle 101, and a working end 104 defining a distal end of the passer 100. Actuator 102 is operatively coupled to a needle (shown in later figures) such that actuation thereof axially slides the needle along the working end 104. As shown actuator 102 is at proximal end of handle 101 and pushing and pulling actuator 102 axially slides needle. In other embodiments, actuator 102 may be a slide disposed along a lateral surface of handle 101, or a lever extending from the static handle body. Actuator 102 may be operatively coupled to a biasing member such that needle remains in an axially retracted configuration unless actuator 102 is actuated. Release of actuator 102 may return needle to the retracted configuration.

Figure 6A:
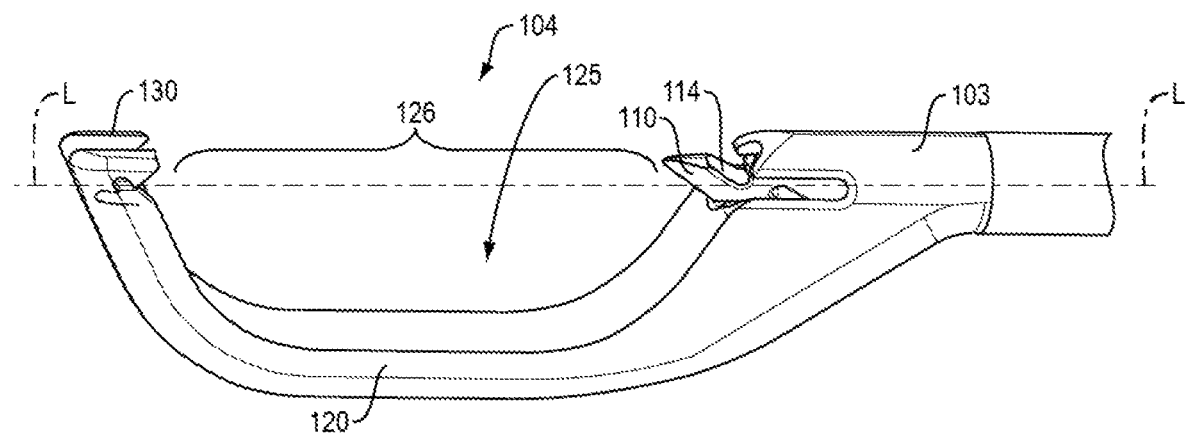
FIG. 6A illustrates a working end of the suture passer, in a suture receiving configuration in accordance with this disclosure.

FIGS. 6A-6M illustrate a working end embodiment of passer 100 and operation thereof. Beginning with FIG. 6A, working end 104 includes a jaw 120 that may be hook shaped. Jaw 120 extends from a distal end of shaft 103. Jaw 120 extends away from a longitudinal axis L-L of shaft 103 and then curves back such that a jaw distal end 130 is axially coincident with longitudinal axis L-L of shaft 103 (as projected). Jaw 120 defines a cavity 125 for receiving tissue therein, the tissue entering through lateral opening 126. Stated from another point of view, working end 104 is hooked under and around tissue to place tissue within cavity 125. In use, tissue such as a first side of a tear or opening may be placed within cavity 125 and a suture passed through the tissue with needle 110. Distal end 130 may cooperate with needle 110 to selectively capture and release suture 8.

FIG. 7A-7D illustrate various views of needle 110. Needle 110 defines a tapered end with a point 112 at a distal most end thereof, configured to pierce tissue. Point 112 may be asymmetrically disposed at a top surface of needle 110. Point 112 is preferably not coincidental with a needle longitudinal axis. Point 112 is disposed on an opposite side of longitudinal axis to second recess 116. Capsule tissue 10 around the hip is especially tough tissue and needle point 112 is configured to pierce the tough capsule tissue during actuation. Extending proximally from point 112 is a ramp 113 that defines a distal facing surface. Ramp 113 may be configured to ride along a length of suture to deflect needle 110, as will be described hereinafter. Ramp 113 is configured to ride along a length of suture without cutting or damaging the suture, and therefore ramp 113 may include edges 113a that are smooth or rounded.

Needle 110 includes two recesses 114, 116 for holding and manipulating suture 8. First recess 114 is distal of second recess 116. First recess 114 maybe on a first or top side of needle 110, while the second recess 116 is on a second different side of needle 110 to first recess 114. First recess 114 may extend from top side surface 110a while second recess 116 may extend from a bottom side surface 110b of needle 110. First recess 114 is configured to advance suture 8 distally through the target tissue disposed within cavity 125, while second recess 116 is configured to withdraw the suture 8 proximally through the target tissue. As such, the first recess 114 may define a distal facing push surface 214*a* that may be concave to partially encircle suture 8. First recess 114 may also define a proximal facing ramp surface 214*b*, configured to guide the suture 8 out of recess 114 upon withdrawal of needle 110 proximally. Second recess 116 may be axially spaced from first recess 114. Second recess 116 may be axially and proximally spaced from first recess 114. Second recess 116 may define a proximally facing pull surface 216*a* that may be concave to partially encircle or hook around suture 8. Second recess 116 may define a distal facing ramp surface 216*b*, configured to guide or funnel the suture 8 into recess 116. Needle 110 may include a larger cross section proximal end 118*a*, proximal of the two recesses (114, 116). This may improve the overall stiffness of needle 110, required to resist deflection of the needle 110 as it is pushed through the tissue. Needle distal end 118*b* may be narrower in profile to fit through a channel 140 in jaw distal end 130

Figure 6B:
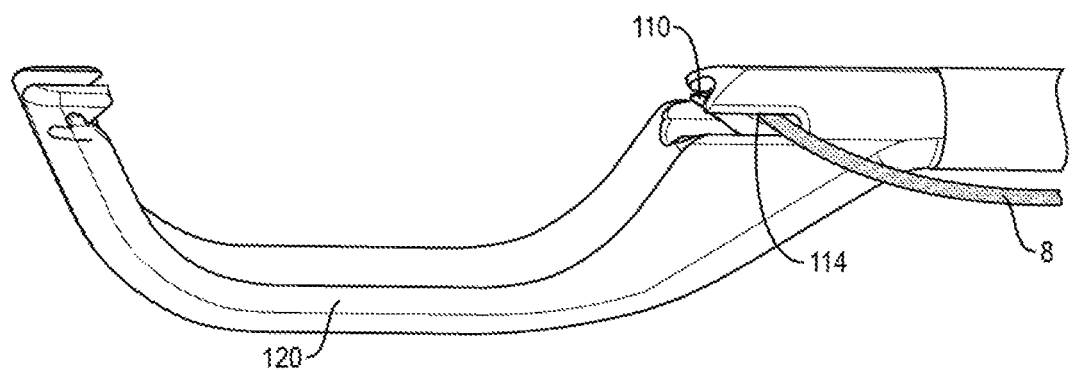
FIG. 6B illustrates a working end of the suture passer, in a suture holding configuration, in accordance with this disclosure.
Figure 6C:
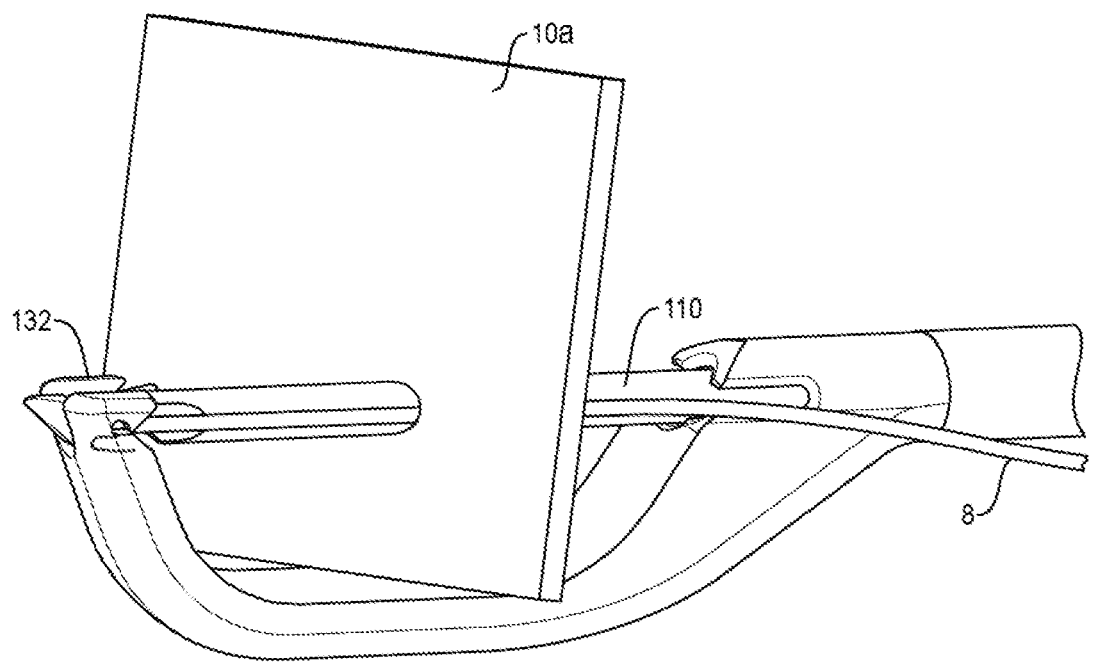
FIG. 6C illustrates a working end of the suture passer, with the needle and suture passed through tissue, in accordance with this disclosure.

Returning to FIG. 6A, needle 110 is illustrated in a first configuration, for receiving a length of suture 8 within first recess 114. Needle 110 extends along a lumen of shaft 103 and is operatively coupled to actuator 102. FIG. 6B illustrates needle 110 in a second configuration, wherein the needle 110 is retracted into shaft 103 to cover recess 114 and retain suture 8 within recess 114. In this second configuration, the working end 104 may be inserted through a port, towards the target tissue. In this second configuration the working end 104 may hook around a first side of a tissue opening to place tissue into cavity 125, while retaining the suture 8 within recess 114. Once in position, the needle 110 may be advanced, distally through a first side of tissue, such as first leaflet 10*a*. While advancing, surface 214*a* pushes suture 8 through leaflet 10*a* and into a cleat 132 of jaw distal end 130, shown in FIG. 6C.

Figure 6D:
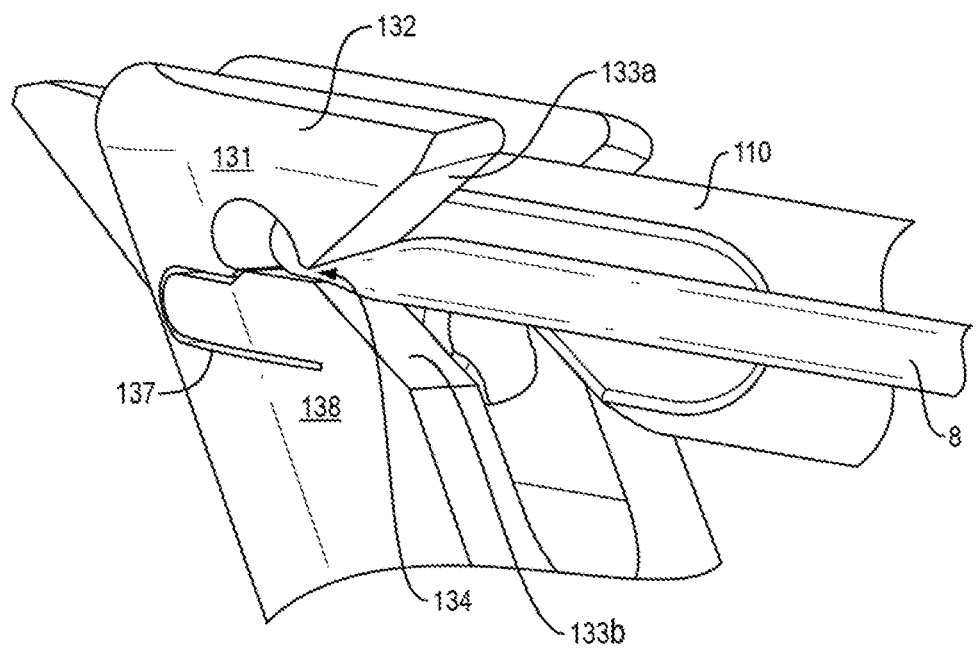
FIGS. 6D-6E illustrates various views of a distal end of working end, with the suture captured within the cleat, in accordance with this disclosure.
Figure 6E:
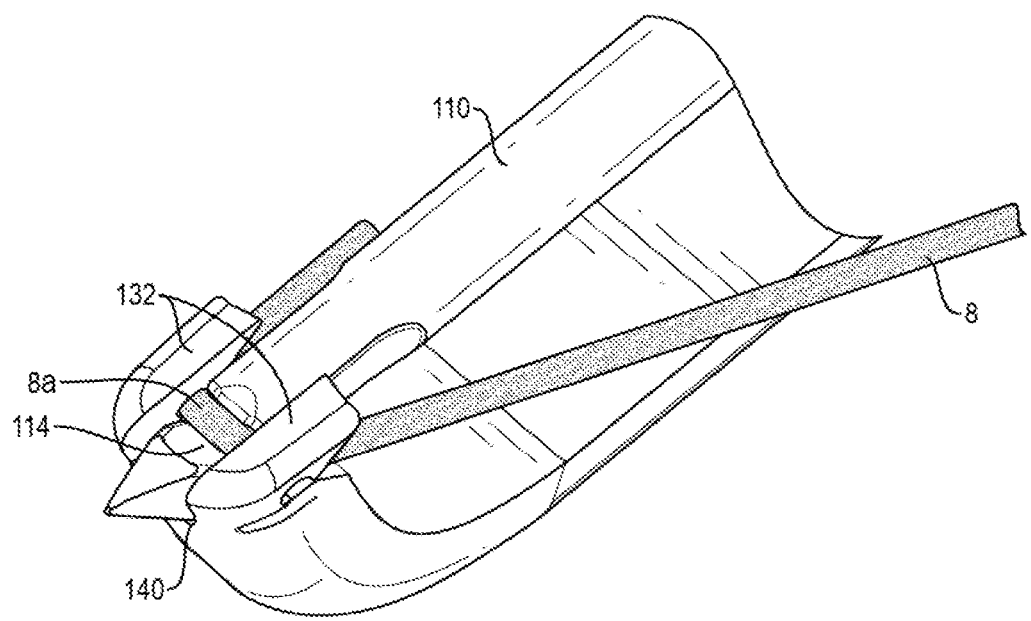
Figure 6F:
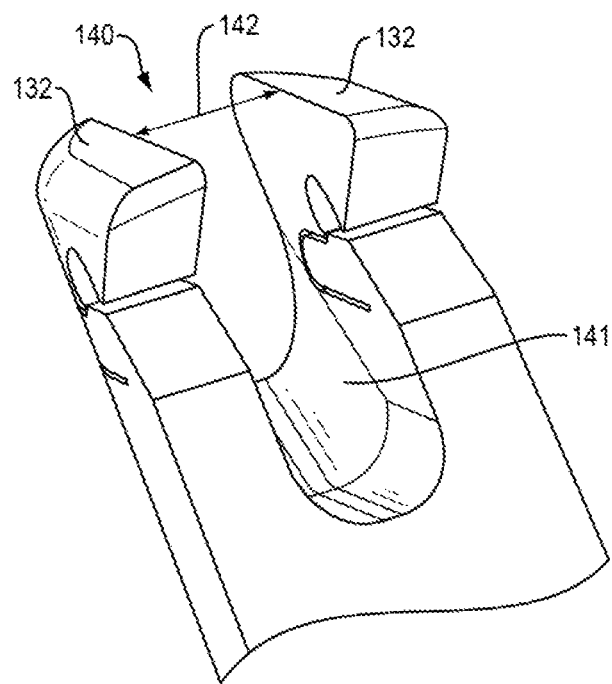
FIG. 6F illustrates a channel of the working end, in accordance with this disclosure.

FIGS. 6D and 6E illustrate further views of suture 8 trapped in cleat 132. Cleat 132 includes a base 138 and spring arm 131 with a suture holding opening 134 therebetween. Base 138 and spring arm 131 may each define proximal facing ramps 133*a* 133*b* to guide suture 8 towards opening 134. Base 138 may include a relief 137 that may be serpentine in shape. Relief 137 is configured to define flexing characteristics of spring arm 131. There may be two cleats 132, laterally disposed from each other, to capture suture 8 either side of needle 110. Cleats 132 are configured to capture suture 8 as needle recess 114 pushes the suture 8 into a channel 140 between cleats 132, seen best in FIG. 6E. Suture 8 is preferably pinched within cleat 132. Suture 8 is preferably pinched within opening 134 with sufficient hold such that retraction of needle 110 does not release suture 8 from cleat 132. Suture 8 forms a suture bridge 8*a* that extends across channel 140, held by the cleats 132. Recess ramp surface 214*b* is configured to guide suture 8 to slide out of recess 114 upon retraction of needle 110. Ramp surface 214*b* may engage suture 8 captured between the two cleats 132 such that retraction of needle 110 may deflect needle 110 deeper into the channel 140 towards channel bottom surface 141 and away from suture 8. Channel 140 without needle 110 and suture disposed therein is illustrated in FIG. 6F.

Figure 6G:
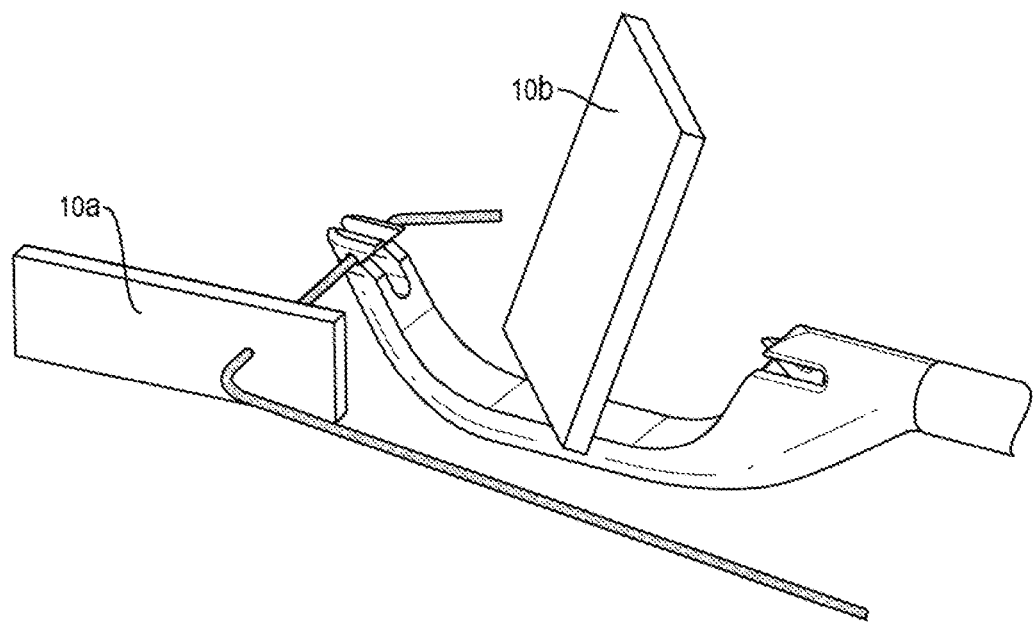
FIG. 6G illustrates a step of moving the suture passer towards a second tissue side while holding the suture within the cleat; in accordance with this disclosure.
Figure 6H:
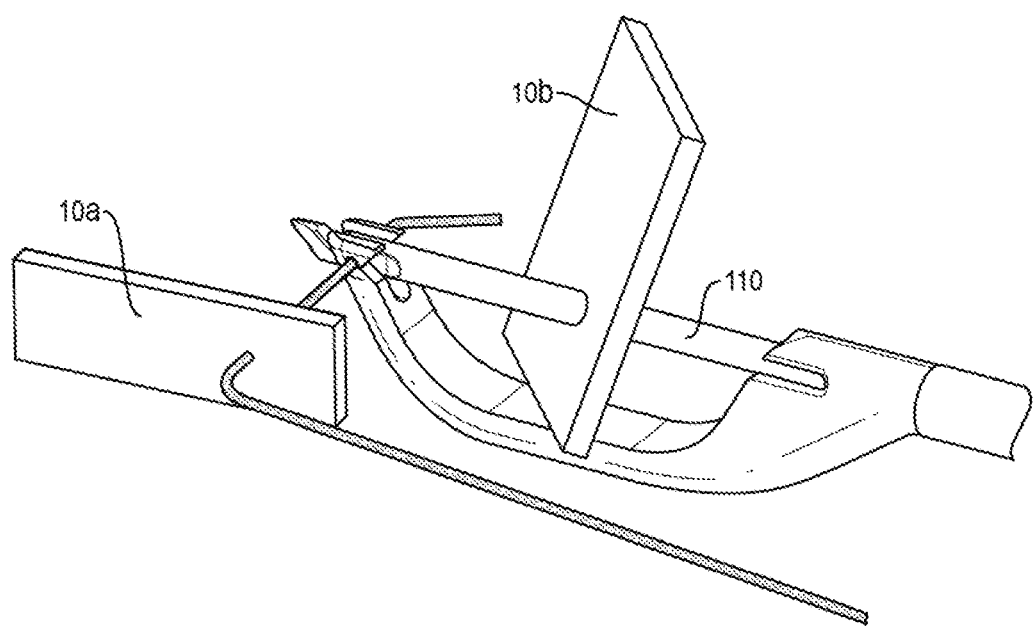
FIG. 6H illustrates a working end of the suture passer, with the needle extended through the second tissue side and capturing the suture bridge in accordance with this disclosure.
Figure 6I:
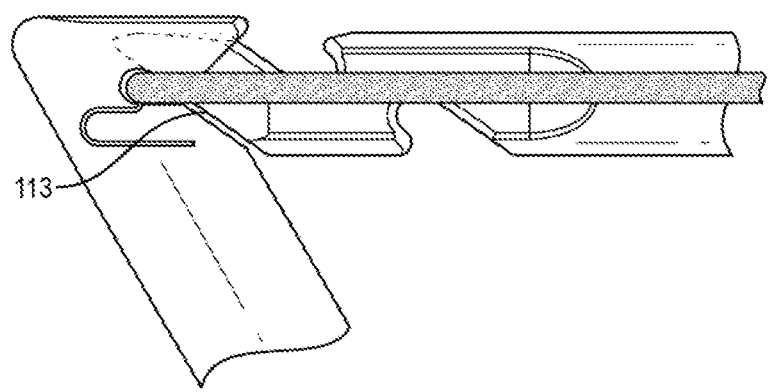
FIGS. 6I-6L illustrates the needle motion as it engages the suture bridge, in accordance with this disclosure.
Figure 6J:
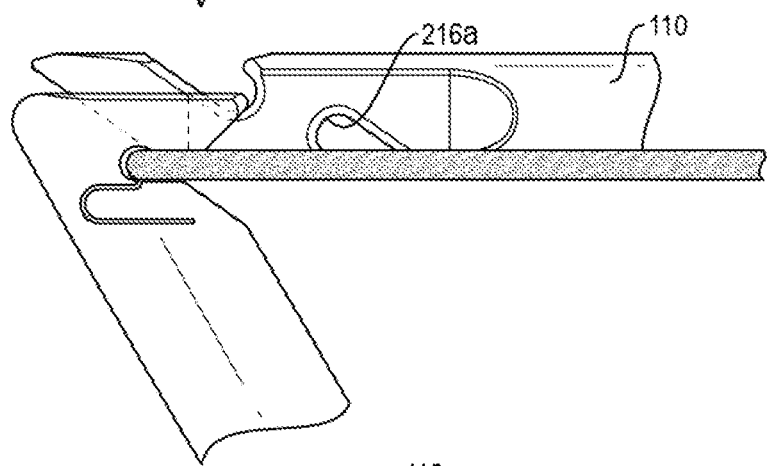
Figure 6K:
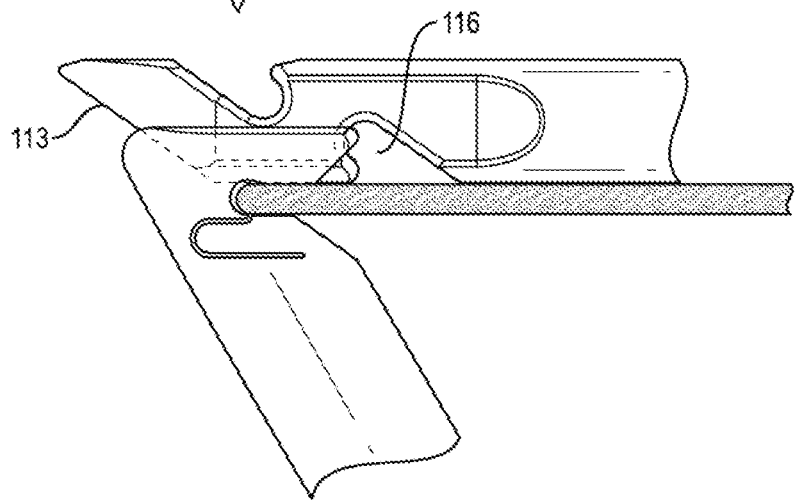
Figure 6L:
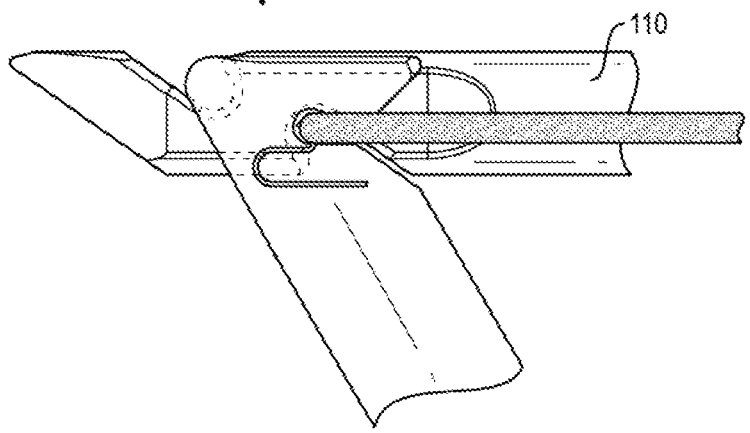

With the suture 8 retained in cleat 132, needle 110 may be retracted back through the tissue 10*a* and towards the first or second configuration (FIG. 6G). Working end 104 may then be moved to hook around second tissue side or leaflet 10*b*. Needle 110 may then be axially advanced, piercing the second leaflet 10*b* to capture suture 8 held within cleat(s) 132, illustrated in FIG. 6H. Capture includes placing the suture bridge 8*a* within the second recess 116. Capture may include advancing the needle 110 such that the distal facing ramp 113 of needle 110 engages the suture bridge 8*a*. Cleat 132 is configured to hold suture 8 with sufficient holding force such that needle 110 deflects away from channel bottom surface 141 and towards opening 142 of channel 140. Ramp 113 is configured to guide deflection of needle 110 over the top of suture bridge 8*a*. FIG. 6I illustrates the ramp 113 engaging suture bridge 8*a*. FIG. 6J illustrates the needle 110 deflecting up over suture bridge 8*a*. FIG. 6K illustrates the needle 110 continuing to advance distally in the deflected configuration sliding over suture bridge 8*a*. FIG. 6L illustrates the needle 110 sprung back towards a neutral configuration (less deflected) as recess 116 becomes axially coincident with suture bridge 8*a*. The suture 8 is now captured within needle recess 116. Recess 116 is configured to remove suture from cleat(s) 132 upon retraction of needle 110. Concave surface 216*a* is configured to engage suture sufficiently to remove suture 8 from cleat(s) 132.

Figure 6M:
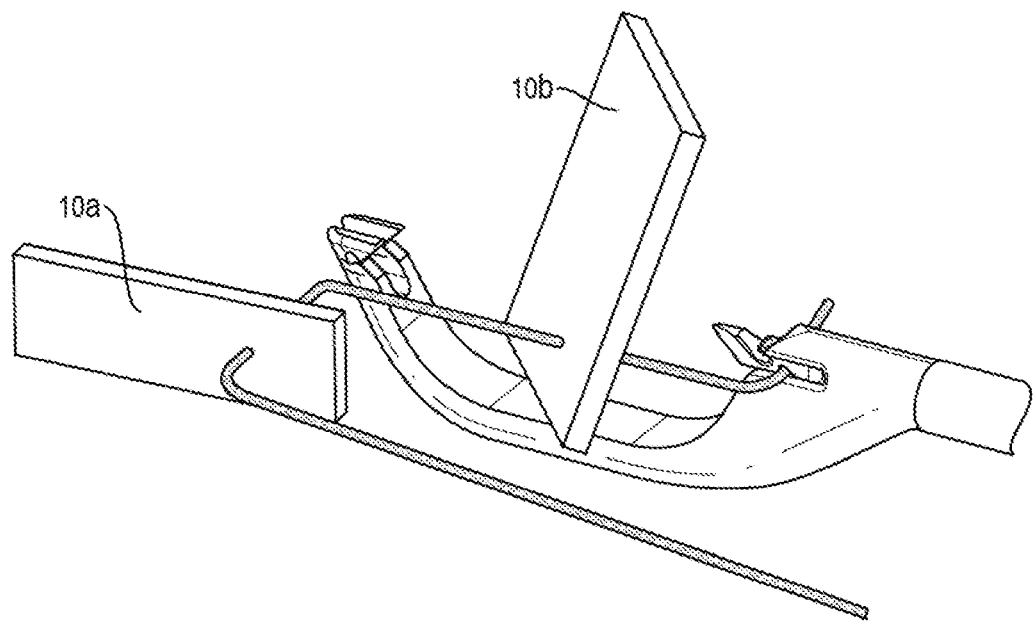
FIG. 6M illustrates the step of retracting the needle through the second tissue side, in accordance with this disclosure.
Figure 6N:
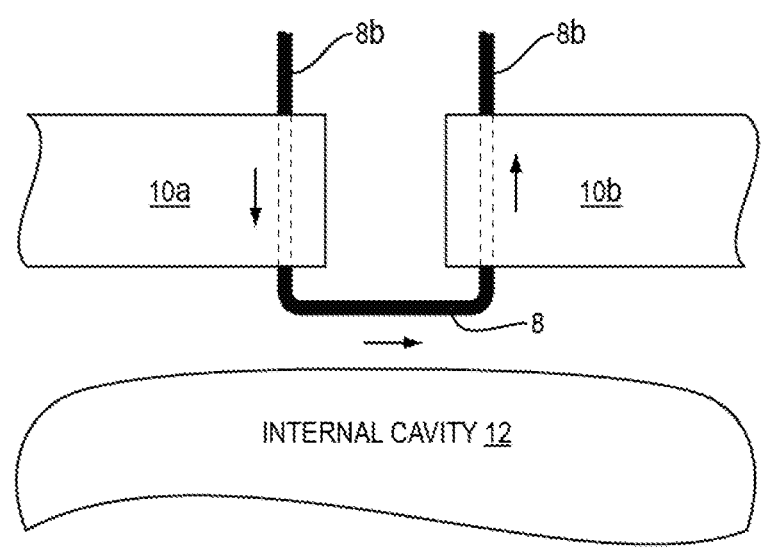
FIG. 6N illustrates the path of the suture through the two tissue portions, in accordance with this disclosure.

Needle 110 may now be retracted to draw suture 8 through second tissue 10*b*, as illustrated in FIG. 6M. FIG. 6N illustrates the two leaflets of tissue 10*a*, 10*b*, with the suture and direction of suture path therethrough. The two ends of suture 8*b* may then be tensioned to oppose the two sides of tissue (10*a*, 10*b*) and then coupled to each other for form a fixed suture loop size. This is also illustrated in FIG. 3 and may forms a complete loop around opening 20. Advantageously, working end may slide distal end 130 under the leaflets and along the inner surface 4 without encroaching into joint 12. Advantageously, working end may move from the first leaflet 10*a*, to the second leaflet 10*b* without requiring removal from the joint area. Jaw 120 may remain extending though opening 20 between the two passes.

FIG. 11A-11F illustrates another example embodiment and method of use of a working end 1104 of a suture passing instrument, similar to working end 104. Like components have been given the same reference numerals. FIG. 11A-11F illustrate working end 1104, and the handle end may be similar to that shown in FIG. 5. Working end 1104 may be the same as working end 104 and instrument 100, with the addition of an axially sliding retainer 1150. Retainer 1150 is configured to slide between an axially retracted configuration and axially advanced configuration. The axially retracted configuration is shown in cross section in FIG. 11A. In this configuration the retainer 1150 is recessed away allowing the needle 110, so that needle may extend into and out of the channel 140 unencumbered by the retainer 1150. The axially retracted configuration is a stored configuration. Retainer 1150 may extend within or along a channel or lumen through the jaw 1120. Retainer 1150 may be a rod or wire that is flexible, sufficient to curve around hook shape of jaw 1120. Retainer 1150 however is sufficiently stiff to be pushed distally into the channel 140. Retainer 1150 may extend along a channel or lumen 1122, formed through jaw 1120 which may partially support retainer 1150 and help direct the trajectory of retainer 1150. Retainer 1150 proximal end may extend along shaft 103 and be operatively coupled to an actuator on the handle, that slides retainer 1150 axially. Retainer actuator may include a stop or means of limiting axial extent of retainer 1150 from the retracted configuration to the axial advanced configuration.

Figure 11A:
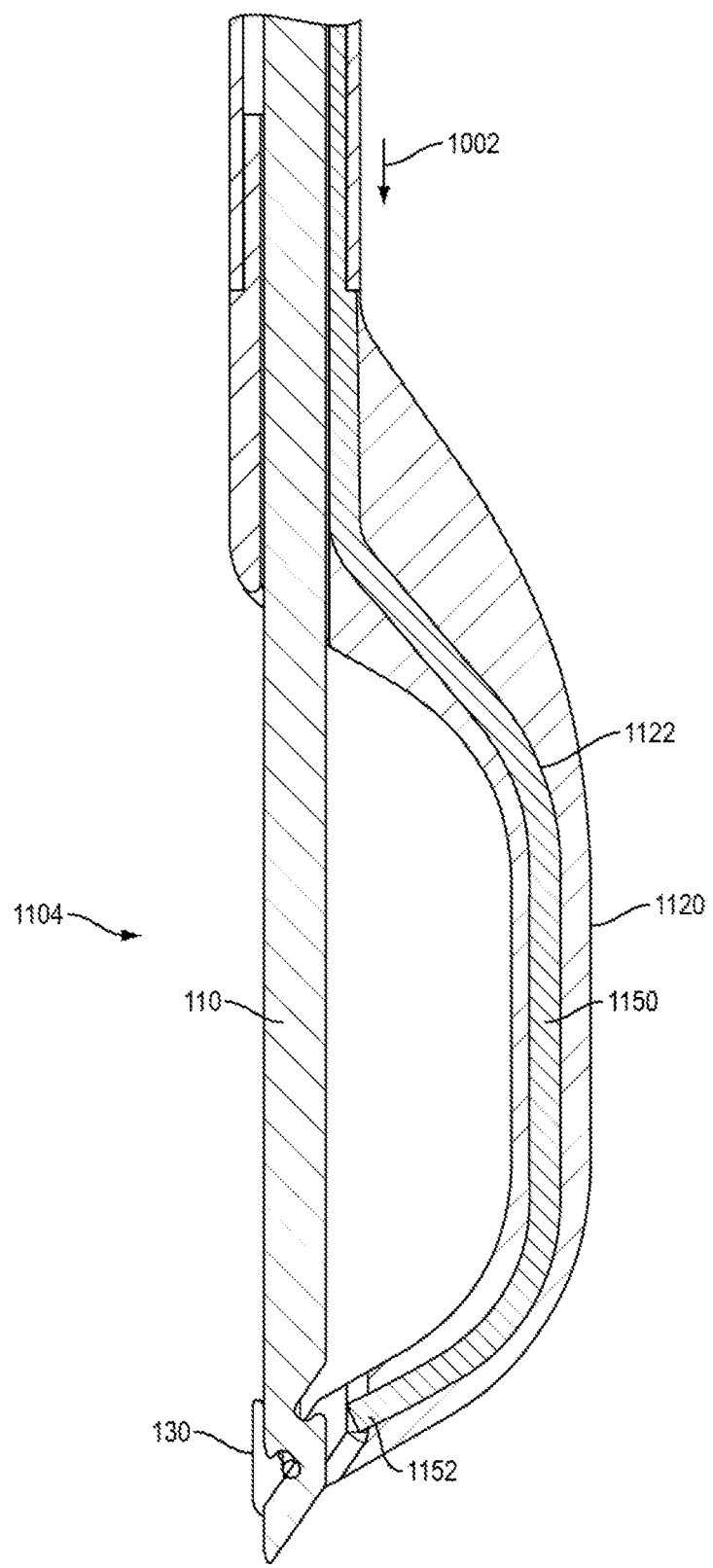
FIGS. 11A-11F illustrate various views and methods of use of a working end of a suture passer, in accordance with this disclosure.
Figure 11B:
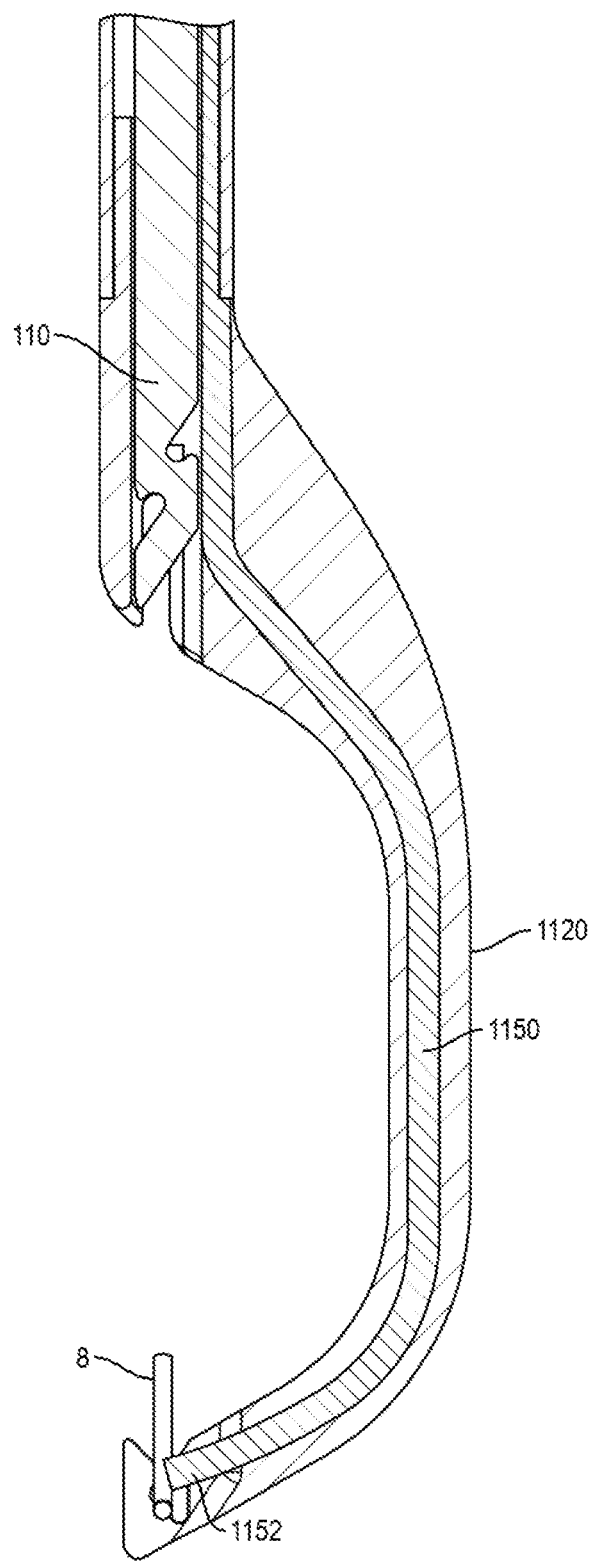

An axially advanced configuration is shown in cross section in FIG. 11B. In this position, retainer distal end 1152 may partially cover or engage the suture bridge 8*a*, best seen in FIG. 11C. In some embodiments retainer distal end 1152 may cooperate with cleats 132 to retain suture 8 within distal end 130. In some embodiments, retainer may form a pulley surface to retain the suture at the distal end 130. In some embodiments, retainer may engage and pinch the suture to retain the suture at the distal end 130. After needle 110 has placed the suture 8 within cleats 132, the needle 110 may then be withdrawn and the retainer 1150 axially advanced to engage the suture bridge 8*a* and help retain the suture within the cleats 132. The retainer 1150 may be axially advanced before withdrawing the needle 110. In other embodiments, not shown, cleats may be avoided and distal end 1152 alone may retain suture 8 at distal end 130. After needle 110 has advanced to a distal most position, the retainer 1150 may be axially advanced to engage the suture 8 with channel 140 and then the needle 110 may then be withdrawn over end 1152.

Figure 11C:
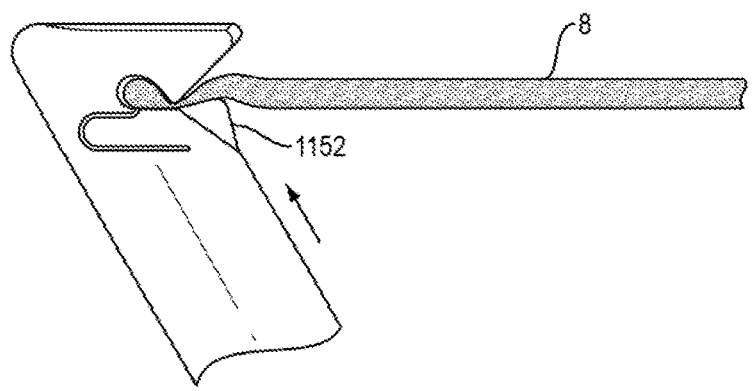
Figure 11D:
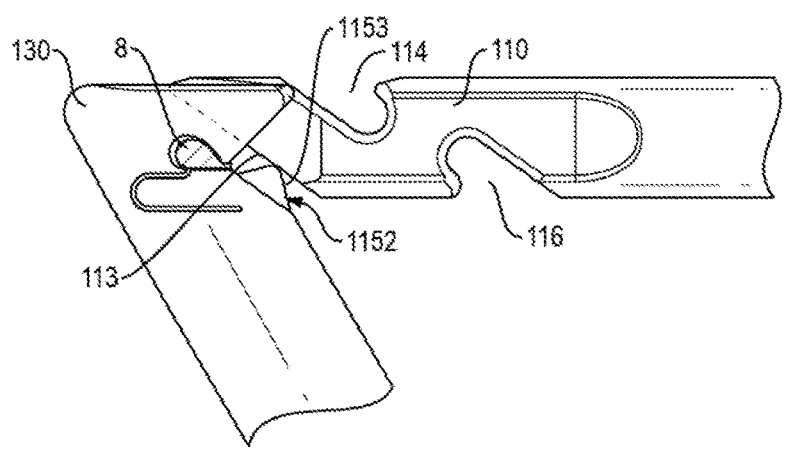
Figure 11E:
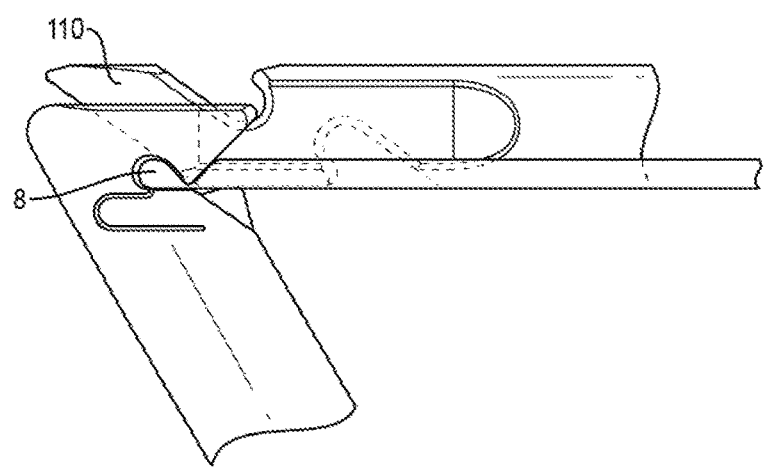
Figure 11F:
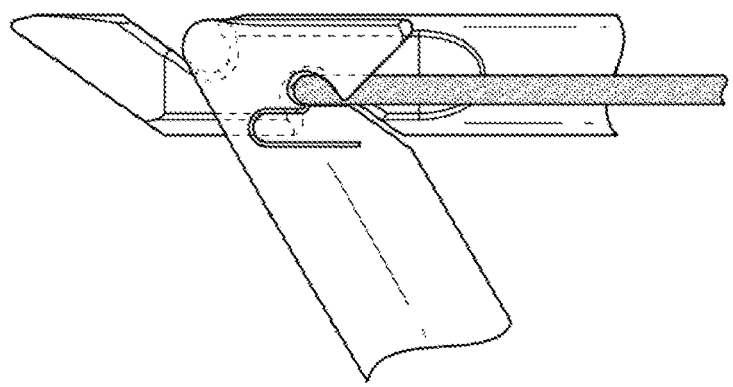

The passer 1100 may then be repositioned to the second side of tissue opening with the retainer 1150 in the axially advanced configuration. FIG. 11C illustrates a view of suture 8 pinched by retainer distal end 1152. Once passer 1100 has engaged a second side of tissue 10*b*, needle 110 is advanced again to capture suture bridge 8*a* with the second recess 116. Retainer 1150 may remain in the axially advanced location during this step. The distal facing ramp surface 113 of needle 110 may first engage a proximal edge or surface 1153 of retainer 1150. As needle 110 continues to advance, this surface 1153 may initiate deflection of needle 110 at least partially over suture bridge 8*a*. Needle 110 may be linear and extend along longitudinal axis of passer shaft 103 when in a relaxed or non-deflected configuration. Deflection bends the needle distal end away from this longitudinal axis. FIG. 11D illustrates needle ramp surface 113 as it axially advances and engages edge or surface 1153. FIG. 11E illustrates the needle partially deflected and axially advancing towards suture bridge 8*a*. Further axial advancement of needle 110, similar to the working end embodiment 104, deflects needle 110 out of channel 140 so as to ride over suture bridge 8*a*. Deflection may be partially directed by edge or surface 1153. Further axial advancement into the channel 140 may cause further needle deflection away from the longitudinal axis via interaction between the suture bridge 8*a*. Suture bridge 8*a* preferably engages needle 110 to limit any relaxation back towards the longitudinal axis as the second recess 116 slides to be axially coincident with surface 1153. This may avert snagging between second recess 116 and edge or surface 1153. Once second recess 116 is axially coincident with suture bridge 8*a*, needle 110 may drop back into the channel 140 and capture suture 8 within recess 116. This is illustrated in FIG. 11F. In other embodiments, retainer 1150 may be axially withdrawn to allow needle 110 to capture suture bridge 8*a* within second recess 116.

FIG. 13A-13D illustrates an alternative suture passer 1300 that may pass two portions of a suture 8, sequentially through tissue. Passer 1300 preferably passes the two portions without having to remove the passer distal end from the opening 20 between passes. Similar to the previous embodiments, passer 1300 includes a handle end with at least one actuator for operating a needle along the passer working distal end 1304. Working end 1304 includes a jaw 1320 that may be hook shaped. Jaw 1320 extends from a distal end of shaft 1303. Jaw 1320 extends away from a longitudinal axis L-L of shaft 1303 and then curves back such that a jaw distal end 1330 is axially coincident with longitudinal axis L-L of shaft 1303 (as projected). Jaw 1320 defines a cavity 1325 for receiving tissue therein, in a similar manner to embodiments 1000 and 1200. Distal end 1330 may cooperate with needle 110 to release portions of suture 8. In this embodiment two lengths of suture 1308*a*, 1308*b* are retained in the distal end 1330 and withdrawn sequentially proximally through the target tissue.

Figure 13A:
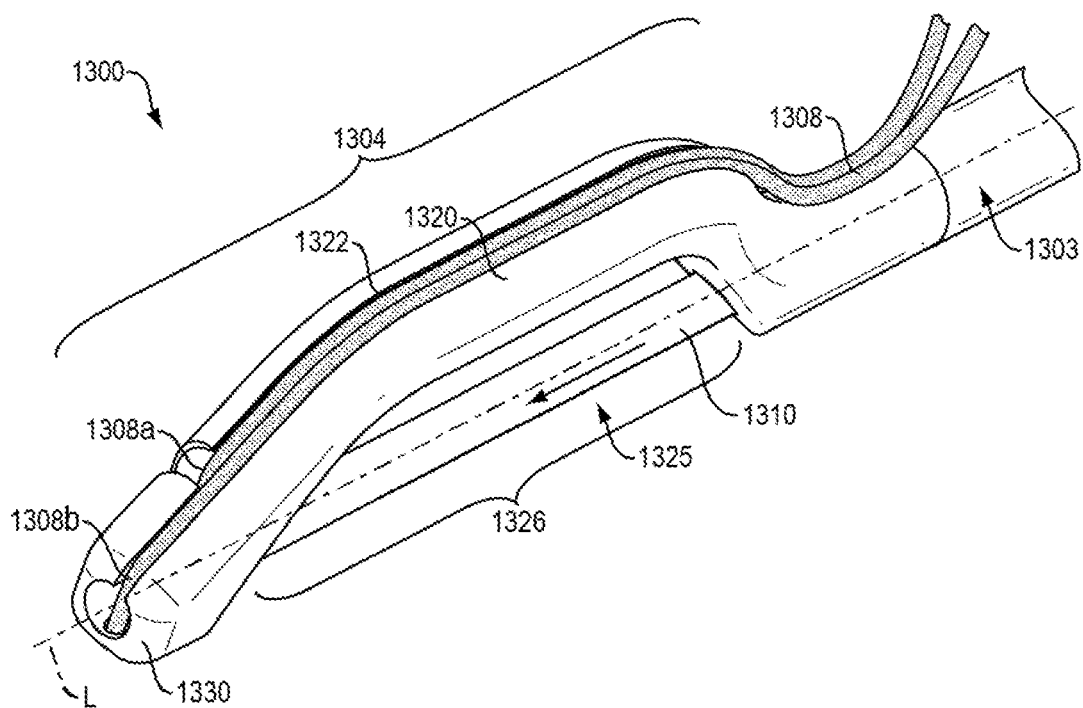
FIGS. 13A-13D illustrate various views of a working end of a suture passer, in accordance with this disclosure.
Figure 13B:
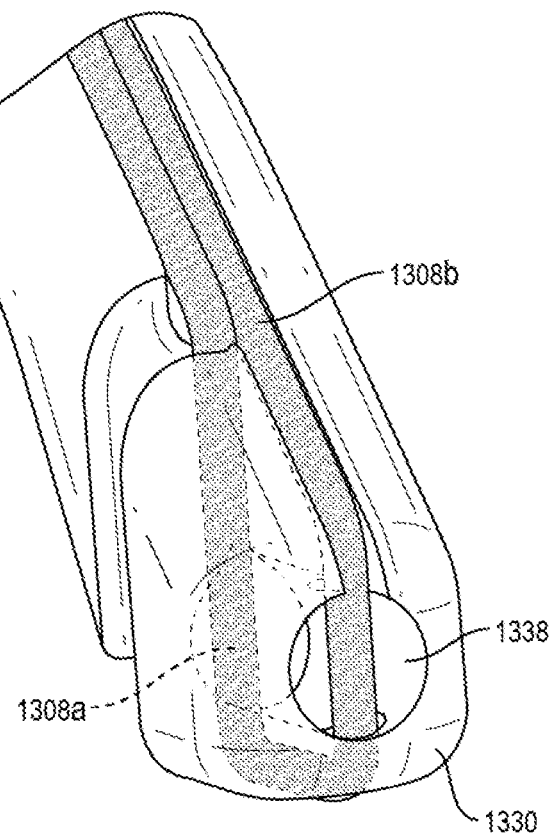
Figure 13C:
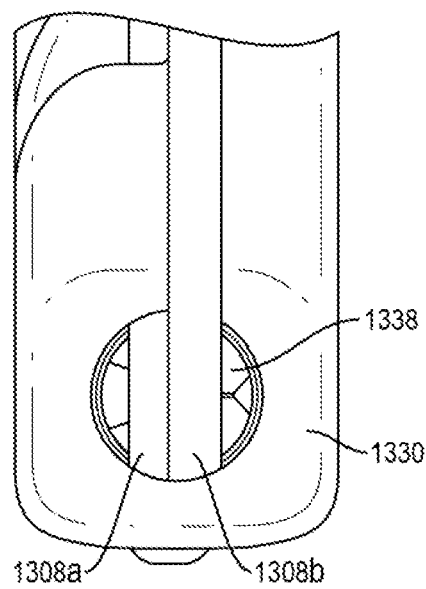
Figure 13D:
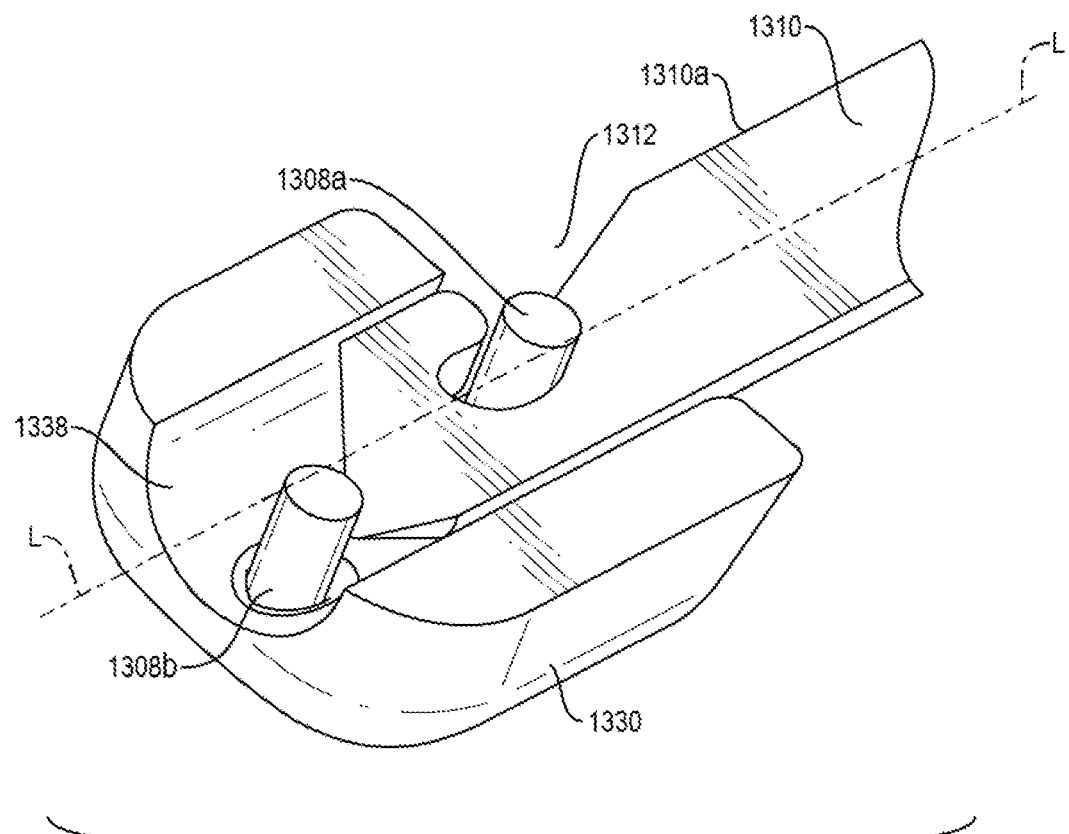

Illustrated in FIG. 13A, jaw 1320 may include an external channel 1322. Suture 1308 is retained and looped around the distal end 1330 defining a first and a second limb 1308*a*, 1308*b*. Illustrated best in FIGS. 13B and 13C, jaw distal end 1330 includes a through-hole 1338, configured to receive a needle 1310 therethrough. Through-hole 1338 may define an axis coincident with and parallel to shaft longitudinal axis L-L. First limb 1308*a* may extend across a proximal end of through-hole while second limb 1308*b* may extend across a distal end of through-hole 1338. At least one of the first or second limbs 1308*a*, 1308*b* may extend across the through hole 1338, offset but parallel to a plane bisecting the through-hole. The two limbs 1308*a*, 1308*b* may extend across a diameter or width of the through-hole 1338 parallel but offset from each other.

Method of use may include hooking the jaw 1320 through the opening 20 and around a first capsule leaflet 10*a* and advancing needle 1310. Needle 1310 is configured to pierce the capsule tissue. Needle 1310 includes a single recess 1312. Needle recess 1312 is configured to capture a suture disposed on the same side of the longitudinal axis L-L as the recess 1312 is oriented. Needle 1310 is operatively coupled to an actuator that axially slides needle 1310 and also rotate needle 1310 around the needle longitudinal axis to adjust an orientation of a needle recess 1312 relative to the jaw 1320 and the shaft longitudinal axis L-L. For example first limb 1308*a* is captured by needle 1310, while needle is oriented to place recess 1312 on a first side of longitudinal axis of the shaft 1303, the first limb 1308*a* extending through the through-hole 1338 laterally disposed relative to the longitudinal axis L-L also on the first side. Once captured within recess 1308*a*, needle 1310 may be withdrawn to withdraw first limb 1308*a* through the capsule tissue. First limb 1308*a* is withdrawn from an internal surface 4 of capsule tissue to an external surface. First limb 1308*a* may then be released from needle 1310 and passer moved to hook around a second portion (10*b*) of the capsule tissue 10. The needle 1310 may be advanced again and through the second portion of the capsule tissue. Second limb 1308*b* may be captured by needle 1310, while recess 1312 is on a second side of longitudinal axis, that may be opposite of the first side. The second limb 1308*b* extends through the through-hole 1338 laterally disposed relative to the longitudinal axis also on the second side of longitudinal axis L-L. Having a single recess may reduce the needle cross section, and therefore the tissue size that is pierced smaller. Having the limbs (1308*a*, 1308*b*) offset from each other better targets the limb capture with as single recess. For example if the needle is advanced in the first pass too far, the needle 1310 is less likely to inadvertently capture the second limb 1308*b*. Once both suture limbs 1308*a*, 1308*b* have been drawn through the tissue, the limbs extend from an external surface of the capsule tissue. Limbs (1308*a*, 1308*b*) maybe tensioned to close the opening 20 and a knot used to form a continuous loop repair.

The specification now turns to a method of closing or repairing an opening through tissue, using fixation members. As explained herein, for some target sites such as the hip capsule, it is preferable to place the fixation constructs on an external surface of the tissue for a functional repair that does not encroach on the joint and tissue therein. Depending in the anatomy, the approach may also be limited such that the instrument remains substantially on the same external side of the tissue as the fixation member is attached. There may be no path available through the internal cavity or joint (12)

for an instrument to extend through, therefore there is a need for a system and method that approaches the tissue from the external surface and places the fixation members on the same external surface. Fixation members may be all-suture anchors such as anchor disclosed in at least commonly owned U.S. Pat. Nos. 8,795,334, 10,292,697 and 9,962,149 herein incorporated by reference in their entirety. Fixation members may be rigid keys or anchors such as those disclosed in at least commonly owned U.S. patents such as anchor disclosed in at least commonly owned U.S. Pat. Nos. 8,512,375, and 8,888,798 herein incorporated by reference in their entirety.

Figure 4:
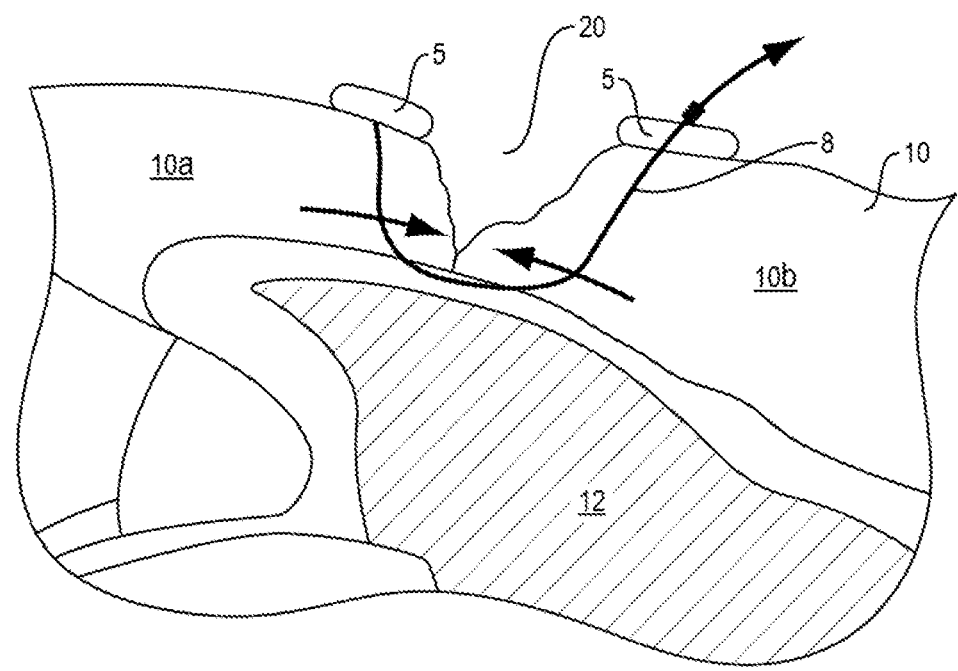
FIG. 4 illustrates a closure repair with fixation devices on an external surface of a hip capsule under load, in accordance with this disclosure.

FIG. 4 illustrates a preferred location of fixation members 5 relative to the hip capsule 10 and opening 20. Internal cavity of joint 12 however includes cartilage, the femoral head and acetabular rim. Access to opening 20 via internal cavity 12 is therefore not readily available. FIGS. 8A-8E illustrate example repair constructs relative to the capsule 10 and opening 20 and methods of locking the construct that place the fixation members 5a, 5b on the external surface 3. In general, repair construct includes two fixation members, a flexible member such as a suture or equivalent operatively coupled to both fixation members and a means of locking the repair, that upon activation prevents the suture 8 from sliding through the fixation members and thereby fixes the two fixation members in place.

Figure 8A:
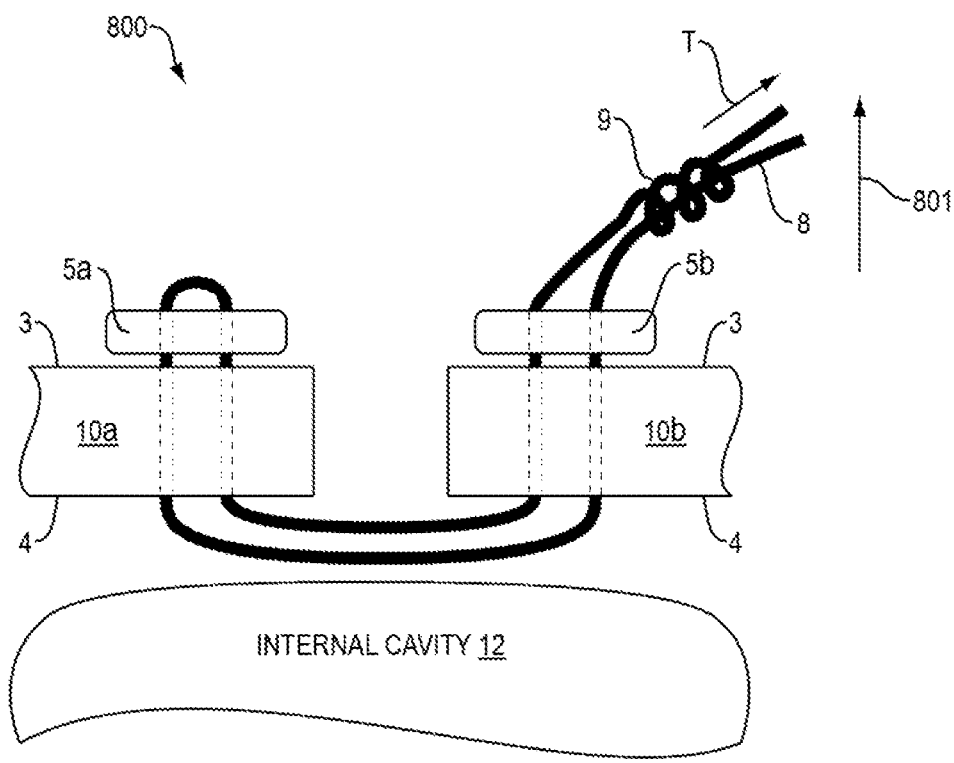
FIGS. 8A-8E illustrate various example repair constructs in accordance with this disclosure relative to two sides of an opening through tissue.

FIG. 8A illustrates a first repair construct 800, in an assembled configuration relative to the tissue. The repair is not yet complete, as the leaflets 10a, 10b are spaced away from each other, and knot 9 is still in a slideable (non-locked) configuration. In the assembled configuration construct 800, including two fixation members 5a, 5b, are disposed on an external surface 3 of the hip capsule 10, a first fixation member 5a engaging an external surface of the first hip capsule leaflet 10a and a second fixation member 5b engaging an external surface of the second hip capsule leaflet 10b. Fixation members 5a, 5b may be all-suture anchors or rigid style key anchors. As illustrated, the construct 800 includes suture 8 formed in a loop and placed through both leaflets 10a, 10b from an internal surface 4 to external surface 3. Two strands of the suture 8 therefore may extend through both leaflets, 10a, 10b. To change the construct configuration from the assembled configuration as shown to a repaired configuration, tension may be applied (T) to the suture limbs. Tension (T) is preferable away from external surface 4, in a direction generally shown by arrow 801. Tension (T) may deploy the fixation devices 5a, 5b. Tension (T) may slide a suture limb to reduce the suture loop length and therefore draw and hold the two leaflets 10a, 10b adjacent or abutting each other. Tension (T) on the suture 8 may cinch a knot 9. Knot 9 may be a sliding knot 9, known in the art that allows the suture loop to reduce and draw the two leaflets 10a, 10b towards each other. Knot 9 may be a Weston Knot, or Tautline hitch knot for example. Once the two leaflets 10a, 10b are in apposition, counter-tension may lock the knot 9. Knot 9 may be in the form of finger trap, formed by extending one suture limb within and along another a lumen of the other suture limb. These are known in the art and may be called a Chinese finger cinch or locking passage. Suture 8 may slide along the suture lumen, until tension T or counter-tension cinches the suture and locks the repair construct 800.

Figure 8B:
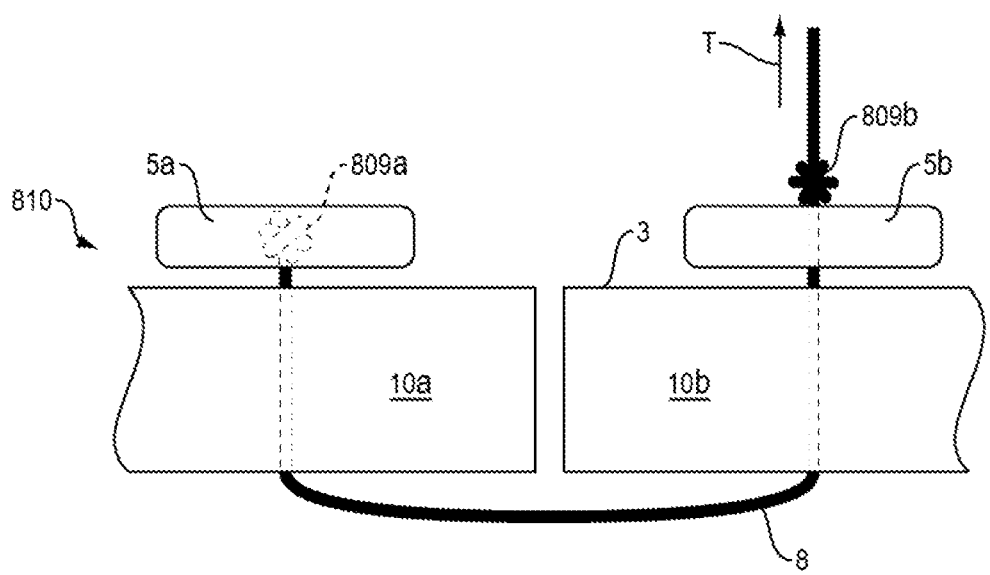

FIG. 8A illustrates a repair construct 800 such that suture 8 forms a loop through both fixation members 5a, 5b and forms a knot 9 at the second fixation member on the external side of the capsule 10. FIG. 8B illustrates another example repair construct 810 including two fixation members 5a, 5b and a single strand of suture 8 extending therebetween. FIG. 8B illustrates a tissue repair in a repaired and locked configuration, with the two leaflets 10a, 10b in apposition, closing the repair and the locking means 809b activated. Suture 8 may be fixedly coupled to the first fixation member 5a, using a knot 809a or adhesive, for example. Suture 8 may be tensioned adjacent second fixation member 5b to complete the repair and a second knot 809b may be formed (or provided pre-formed) to fix the repair construct with the leaflets in apposition. Both knots 809a, 809b may be external to the capsule and on the external side of the repair.

Figure 8C:
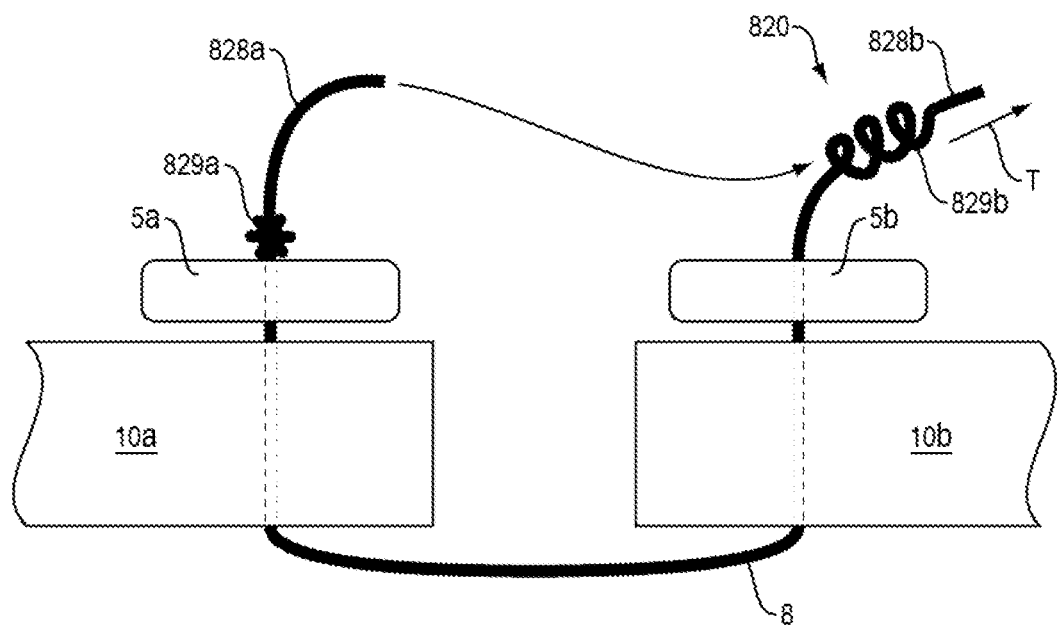

FIG. 8C illustrates another repair construct 820 in an assembled configuration and with the leaflets 10a, 10b not yet placed in apposition. Like construct 810, suture 8 may engage the first fixation member 5a with a knot 829a, or adhesive of other fixing means know in the art. A second knot 829b may be provided at the opposing end of suture 8. Once fixation members 5a, 5b have been placed, suture limb 828a may be operatively coupled to second knot 829b and drawn therethrough. Knot 829b may be a sliding knot known in the art that allows the suture loop to reduce and draw the two leaflets 10a, 10b towards each other. Knot 829b may be a Weston Knot, or Tautline hitch knot for example. This may form a repair with a complete loop, extending across the opening 20 on both an internal surface and external surface of the capsule wall 10. Tension on the first limb 828a may reduce the complete loop, while tension on the second limb 828b may lock the knot 829b around first limb 828a.

Figure 8D:
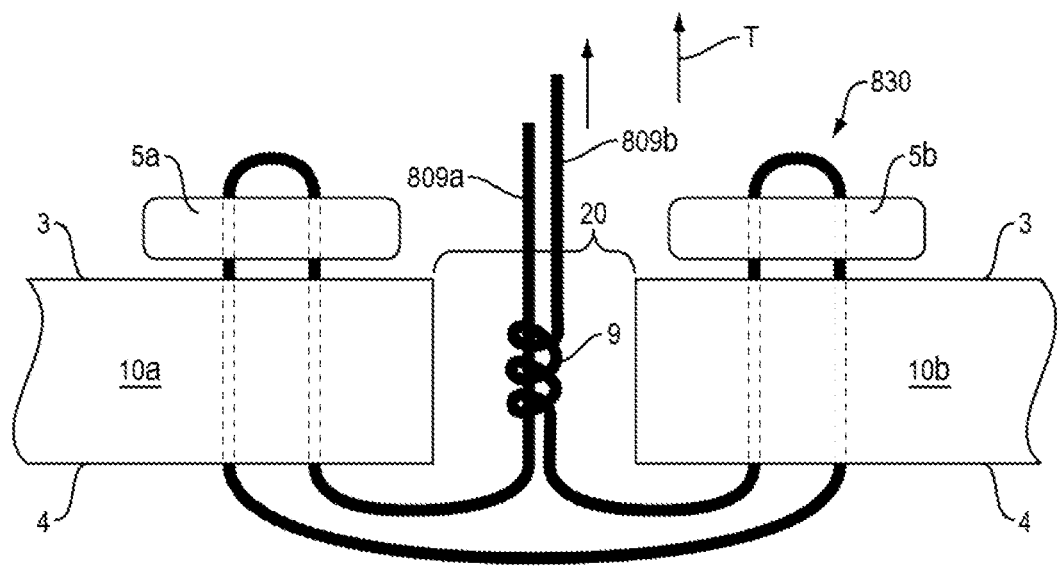
Figure 8E:
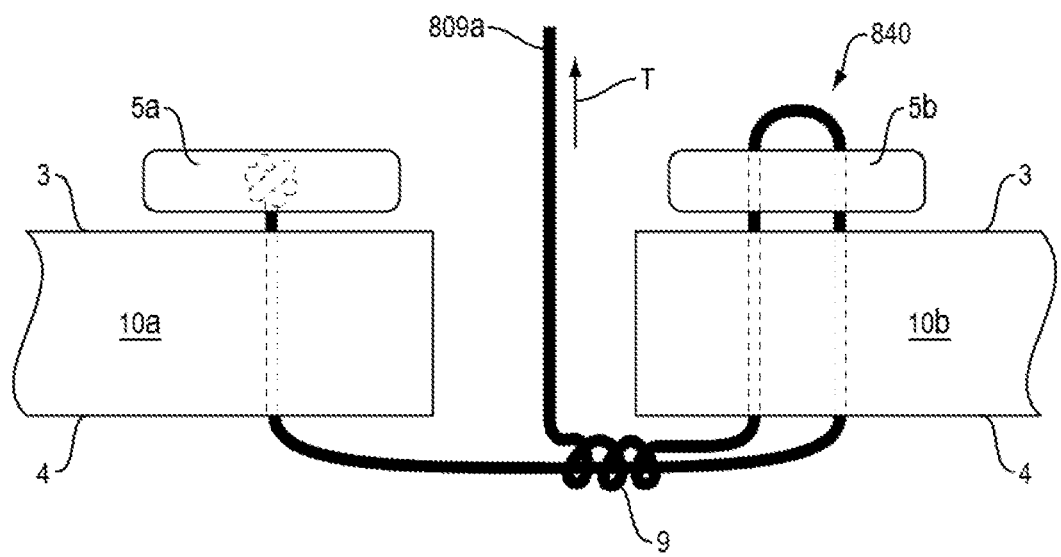

FIG. 8D illustrates another example repair construct 830, with the suture 8 looped through both fixation members 5a, 5b and along internal surface 4. In this construct, knot 9 may be disposed between both fixation members 5a, 5b, with the limbs 809a, 809b extending through opening 20. Like previous constructs, Tension T may deploy fixation members 5a, 5b and close the opening 20. In the repaired configuration, knot 9 may be disposed on an internal surface 4 of the capsule. FIG. 8E illustrates another example repair construct 840, with the suture 8 coupled to the first fixation member 5a and looped through the second fixation member 5b and along internal surface 4. In this construct, knot 9 may be disposed between both fixation members 5a, 5b, with a single limb 809a, extending through opening 20. Like previous constructs, Tension T may deploy fixation members 5a, 5b and close the opening 20. In the repaired configuration, knot 9 may be disposed on an internal surface 4 of the capsule. Knot 9 may be a sliding knot 9, known in the art that allows the suture loop to reduce and draw the two leaflets 10a, 10b towards each other. Knot 9 may be a Weston Knot, or Tautline hitch knot for example.

Figure 9A:
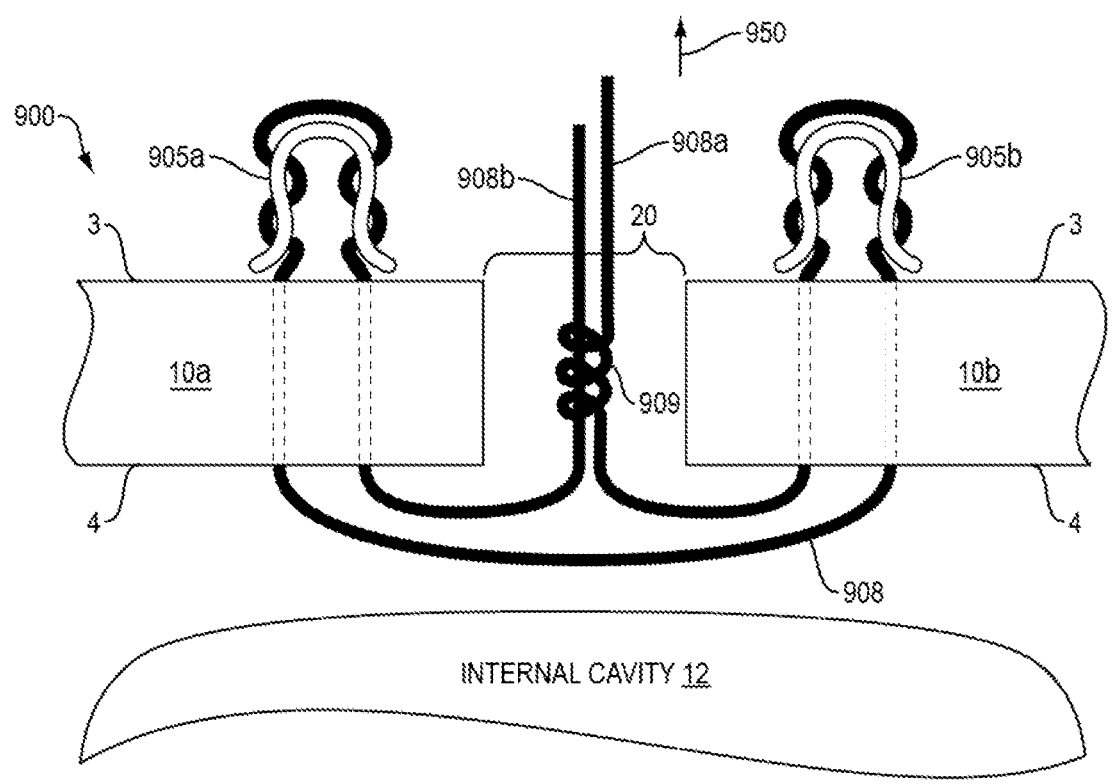
FIGS. 9A-9B illustrate an example repair construct in an assembled and repaired configuration respectively, in accordance with this disclosure.
Figure 9B:
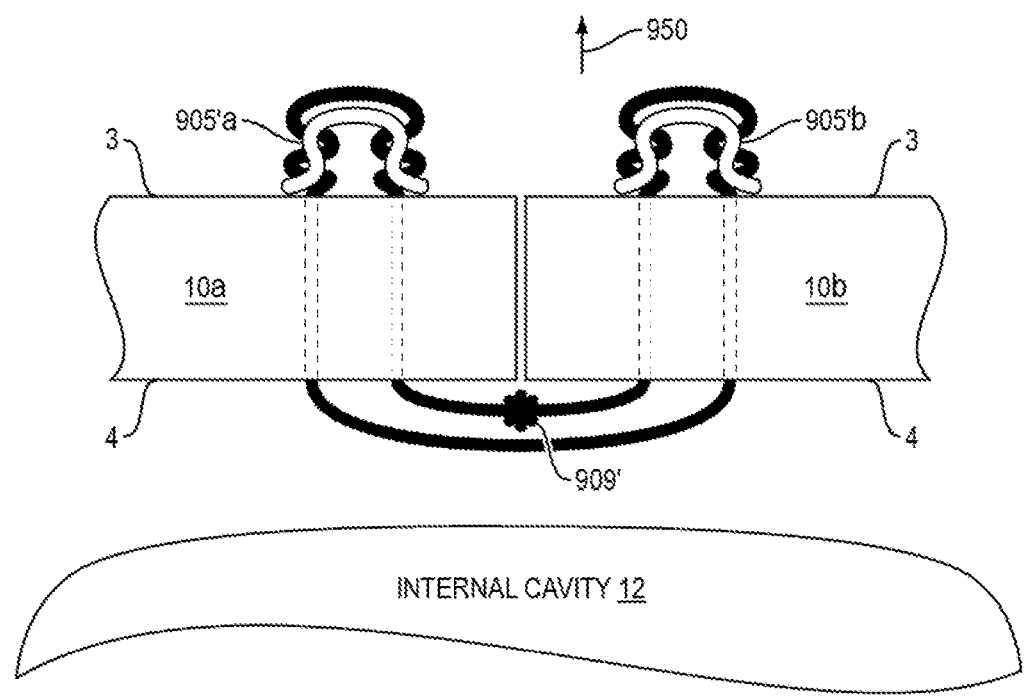

FIG. 9A illustrates a example repair construct 900 similar to construct 830, illustrating the fixation members as all-suture anchors 905a, 905b. FIG. 9A illustrates an assembled configuration. The assembled configuration may be assembled to the capsule 10 but the opening 20 may need to be closed, the fixation members may yet need to be deployed and the repair construct may still be unlocked. Repair construct 900 includes at least one suture 908 operatively coupled to both anchors 905a, 905b and at least one means of locking the repair 909. This means of locking may include a sliding knot or finger trap, similar to those disclosed herein. First anchor 905a may be placed first on an external surface 3 of leaflet 10a. The anchor 905a may be placed with an insertion instrument shaft and handle disposed substantially on the external side of the leaflet 10a (illustrated later) and therefore the internal cavity 12 is avoided. First anchor 905a may be extended through the first leaflet 10a from the internal surface 4 to the external surface 3 to place the first anchor 905a on the external surface 3. First anchor 905a may be in a folded or relaxed configuration while placing the anchor 905a on the external surface 3. First anchor 905a may remain in this relaxed configuration while the second anchor 905b is placed. FIG. 9A illustrates the all-suture anchors 905a, 905b in a relaxed, un-deployed configuration. A suture 908 is operatively coupled to both first and second anchor 905a, 905b. In this method, suture 908 extends from first anchor 905a, through the first leaflet 10a to the internal surface 4 of capsule leaflet 10a and across opening 20. A second anchor 905b may also preferably be the placed on the external surface 3 of second leaflet 10b. Second anchor 905b may be pushed through the leaflet 10b from the internal surface 4 to the external surface 3 to place second anchor 905b on this surface 902. Suture 908 may be operatively coupled to second anchor 905b, and therefore extending the second anchor 905b through the leaflet 10b may also extend the suture 908 through the leaflet 10b. A sliding and locking knot 909 may be provided pre-formed in the suture 908. With the anchors 905a, 905b in place (assembled configuration) as illustrated in FIG. 9A, the suture limbs 908a, 908b may be tensioned to close the tissue opening 20, as illustrated in FIG. 9B. Tension on at least one of the suture limbs 908a, 908b may deploy both anchors 905a, 905b to a laterally expanded and axially shortened form 905a' and 905b'. Tension on at least one of the suture limbs 908a, 908b reduces the suture loop, to draw the leaflets 10a, 10b towards each other and close the opening 20. Tension on the suture 908 may slide suture limb 908b through a loop of knot 909 formed in suture limb 908a. Tension on the suture limbs 908a, 908b may place knot 909 into a locking configuration 909' thereby locking the repair construct 900 and therefore locking the leaflets 10a, 10b, in a closed configuration. Knot 909 may be placed anywhere along suture 908 that allows the suture loop to reduce and then lock the repair. In the embodiment shown in FIGS. 9A and 9B, knot 909 may be disposed on the internal surface 4 of the capsule wall 10, while tension is in direction indicated by arrow 950. At least one of the suture limbs 908a, 908b may extend through the capsule wall to the external side directly adjacent the fixation members. At least one of the suture limbs 908a, 908b may extend away from the joint 12, and tension may be in the direction away from the joint 12 and external surface 3. As explained earlier, access to the space behind the joint is constrained, and therefore tension in the direction into the joint inhibited. Limbs 908a, 908b may be coupled to an insertion tool or system, with a handle. Stated another way, tension may be in a proximal direction from a proximal surface of the tissue, while the knot is on an opposing, distal surface or side of the tissue.

In some example embodiments, the repair construct may include a second sliding knot (not shown) disposed adjacent the first anchor 905a in a similar relationship knot 909 has, relative to the second anchor 905b. Therefore, this construct may include two separate lengths of suture with four suture limbs, two limbs extending from each anchor 905a, 905b. The two lengths of suture may both extend between and along the two anchors 905a, 905b. A first sliding knot may be tensioned and locked, to deploy the first anchor 905a and a least partially close the opening 20. The second sliding knot may then be tensioned and locked, to deploy the second anchor 905b, complete the closure of opening 20 and complete the repair.

FIGS. 10A-10G illustrate various views and a method of use of a system 1000 including an instrument 1010 that may place fixation members (5a, 5b, 905a, 905b) on an external surface 3 of a tissue. This may be particularly advantageous for anatomy where there is limited or no access from the internal or opposing side of the target tissue. System 1000 may include instrument 1010 that may be operatively coupled to a repair construct such as construct 800, 810, 820, 830, 840 or 900. Instrument 1010 includes a working distal end 1015 shown in FIG. 10A. Proximal end (not shown) may include a handle and actuation means that may move portions of the working end 1015. Working end 1015 is configured to engage opposing surfaces of the hip capsule wall and manipulate the repair construct (800, 810, 820, 830, 840, 900).

Shaft 1012 may extend from handle 1005 and may terminate at the working end, with a first jaw 1050 and a second jaw 1020. Jaws 1020, 1050 may both extend parallel to each other and be approximately equal in length. Jaws 1020, 1050 may extend perpendicularly from shaft longitudinal axis L-L. First jaw 1050 is provided housing the repair construct 800, 810, 820, 830, 840, 900. First jaw 1050 is configured to be placed under capsule along the capsule inner surface 4, without intruding into the internal cavity 12. First jaw 1050 may define a stationary jaw, fixedly coupled to shaft 1012. First jaw 1050 may include a pair of jaws, each one of the pair having a similar element to the other. First jaw 1050 may house a pair of slideable needles 1030a, 1030b, each needle 1030a, 1030b housed within its own channel 1053a, 1053b respectively. Each channel is configured to house and guide the corresponding needle as it advances and retracts. Each channel 1053a, 1053b may be covered to help retain a needle in a straightened configuration housed therein. This is preferable while positioning the first jaw 1050 under the capsule tissue. FIG. 10E illustrates a top view of the first jaw 1050 with one of the channels 1053b exposed, illustrating the needle 1030b in a retracted position. First jaw 1050 is illustrated as a single body including the pair of channels 1053a, 1053b. In other embodiments, first jaw 1050 may include two channels 1053a, 1053 that have an axial gap therebetween. First jaw 1050 is illustrated straight but may include an elongate curve to curve around the femoral head within the joint, and better approximate the anatomy. First jaw 1050 defines a coupled end that extends from shaft 1012, and a tip 1051 at the opposite end thereof. Tip 1051 includes a pair of apertures 1052a, 1052b. A first of the pair of apertures in communication with a first channel 1053a for a corresponding needle 1030a to exit and enter the corresponding channel 1053a. The second of the pair of apertures may mirror the first. First jaw 1050 may define a sufficient length to place a fixation member (5a, 5b, 905a, 905b) through the capsule wall at a location spaced necessarily away from the opening edge. Opening edge may be jagged and uneven, therefore jaw length may be at least 5 mm long and up to 25 mm long.

Figure 10A:
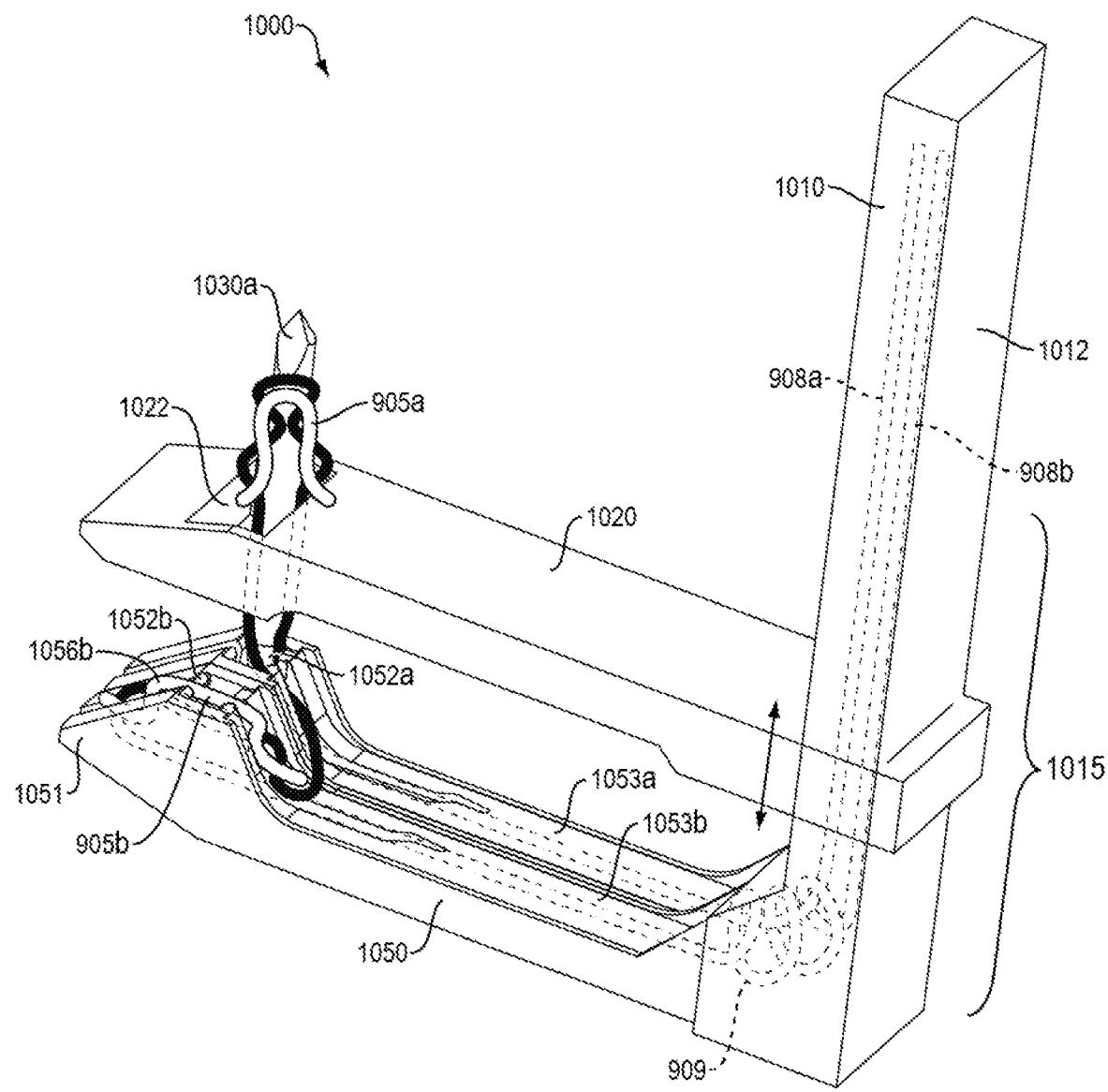
FIGS. 10A-10G illustrate various views and methods of use of a repair system that includes one of the constructs illustrated in FIG. 8A-8E or FIGS. 9A-9B, in accordance with this disclosure.
Figure 10B:
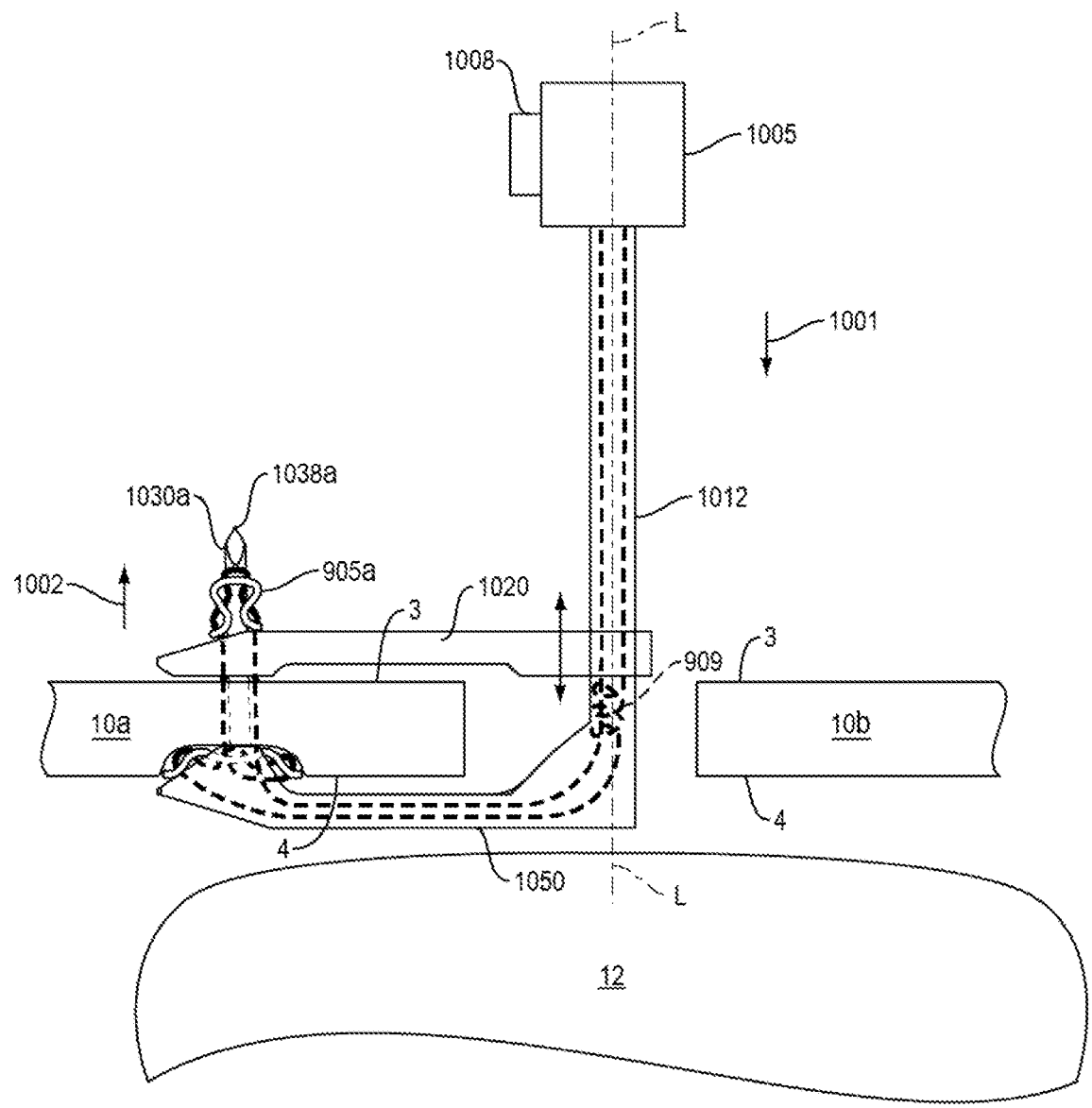
Figure 10C:
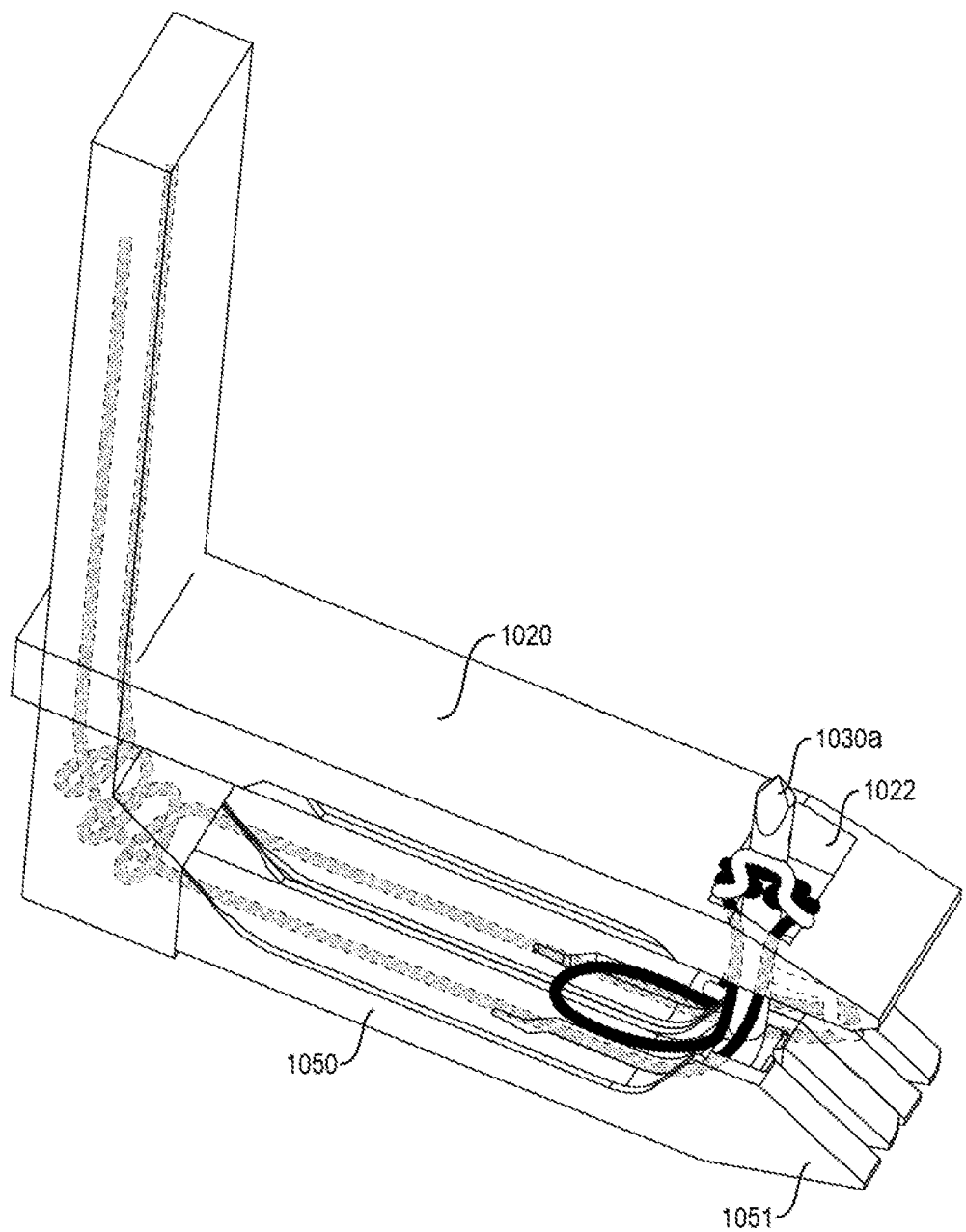
Figure 10D:
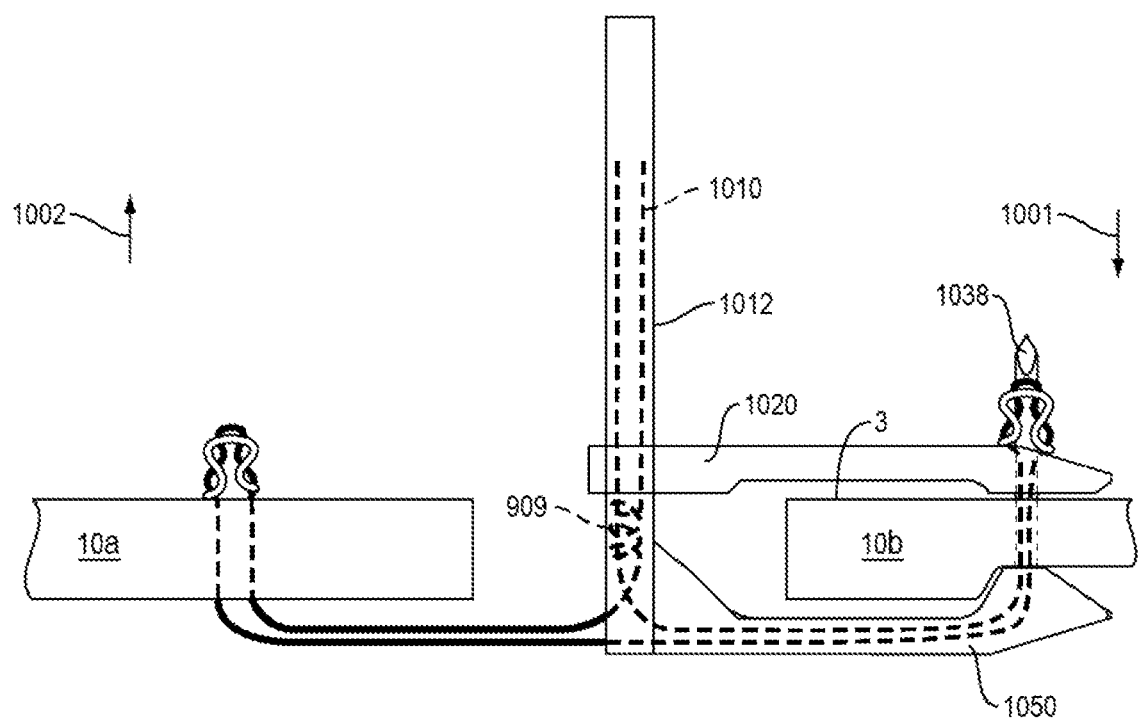
Figure 10E:
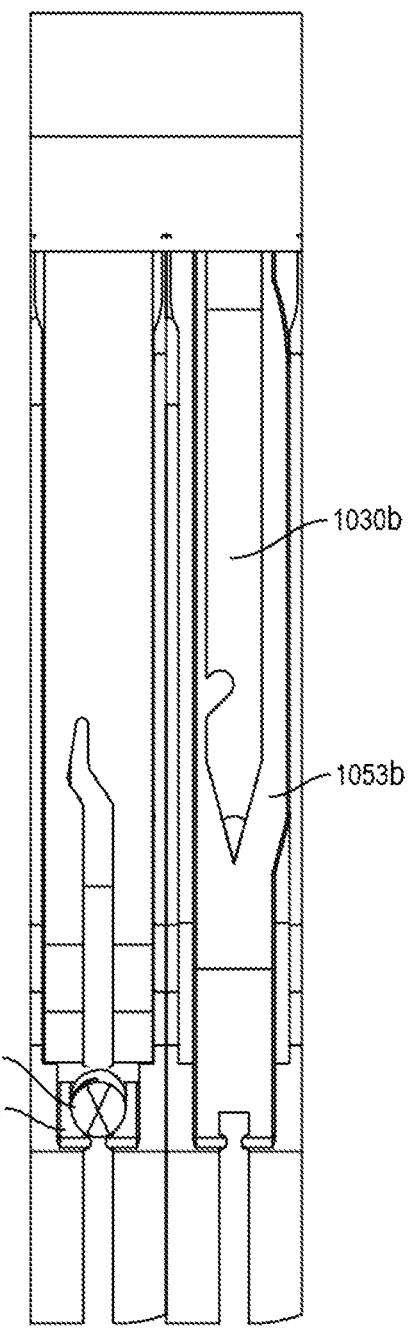
Figure 10F:
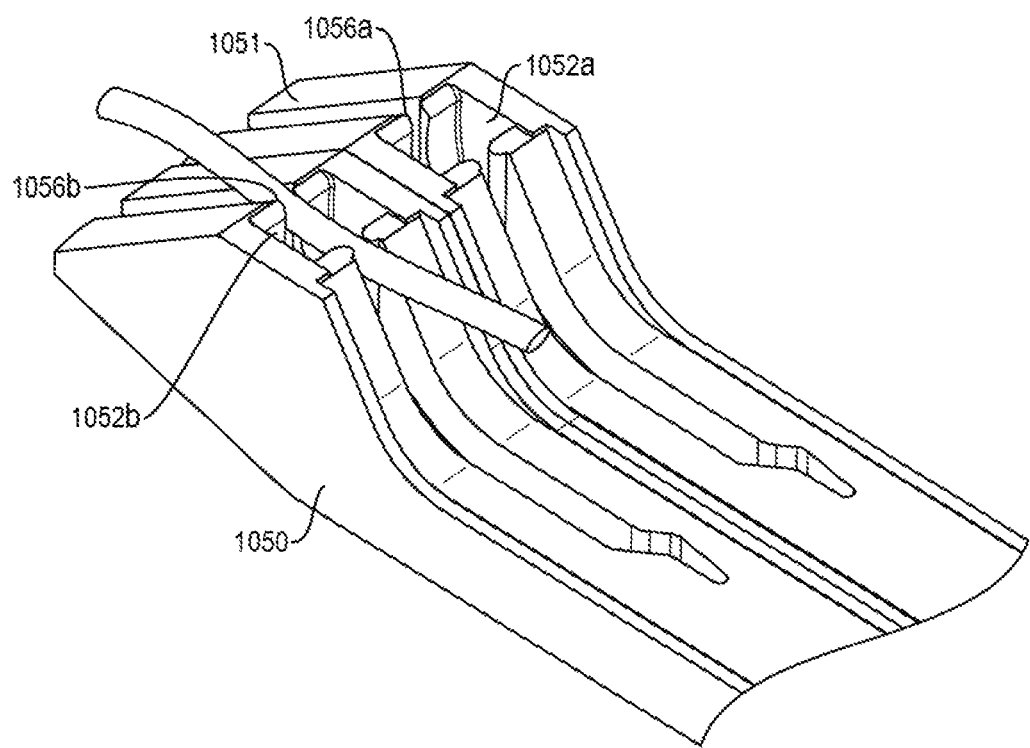
Figure 10G:
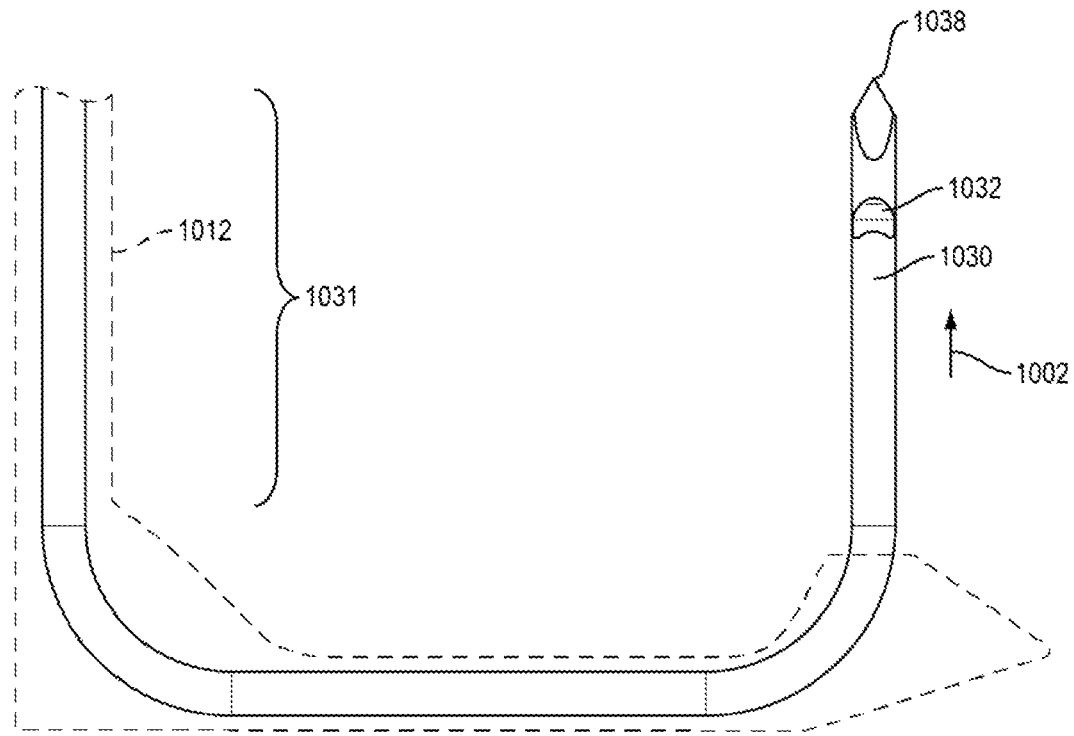

Each aperture 1052a, 1052b may define a boundary, and each boundary may be interrupted by a slot that defines a cleat 1056, best illustrated in FIG. 10F. Cleat 1056 may be configured to hold the fixation member (5a, 5b, 905a, 905b) therein. Each aperture 1052a, 1052b has its own cleat 1056a, 1056b. Each cleat 1056a, 1056b may interrupt a boundary of the corresponding aperture is in two locations, spaced away from each other to hold the fixation member (5a, 5b, 905a, 905b) in two discrete locations. Cleat is configured to orient a fixation member (5a, 5b, 905a, 905b) along the axis of first jaw. Cleat 1056 is configured to releasably hold fixation member (5a, 5b, 905a, 905b) therein, such that advancement of a needle may capture the fixation member and remove the fixation member from the cleat. Each channel 1053a, 1053b may curve adjacent the jaw tip 1051 to guide needle 1030a, 1030b through leaflet in a retrograde, or proximal direction 1002.

Second jaw 1020 may be axially slideable along shaft 1012. Second jaw may be operatively coupled to a push/pull rod (not shown) that extends along shaft 1012 to an actuation means coupled to handle 1005. Second jaw 1020 is configured to axially side and engage the external surface 3 of capsule 10. This may stabilize the leaflet (10a, 10b) to improve needle travel therethrough. Second jaw includes an opening 1022.

FIG. 10A illustrates system 1000 with a first needle 1030a extended between the two jaws (1020, 1050) and through opening 1022 of second jaw 1020. First needle 1030a has engaged fixation member 5a, 905a. Second needle 1030b is still recessed within first jaw 1050 with second fixation member 5b, 905b retained with cleat 1056b. FIG. 10B illustrates system 1000 in the same configuration as FIG. 10A and disposed through tissue opening 20. The steps to reach this position include extending the shaft 1012 through opening 20 to place first jaw 1050 along internal surface 4 of leaflet 10a. The repair construct (800, 810, 820, 803, 840, 900) is retained within the first jaw 1050, with both needles 1030a, 1030b retracted while placing the first jaw 1050 under leaflet 10a. Both fixation members (5a and 5b, or 905a and 905b) may be retained within their respective cleats 1056a, 1056b while placing first jaw 1050 under leaflet 10a. Second jaw 1020 is slid axially to engage external surface 3 of leaflet 10a. Once the leaflet 10a has been engaged, the first needle 1030a may be actuated to first engage a portion of the repair construct (800, 810, 820 900), remove the fixation member 5a, 905a from the cleat 1052a and push the fixation member towards the external surface 3. Actuation may be via a lever or sliding button 1008 on handle 1005. Actuation may slide a push rod within shaft 1012 in a first direction 1001 to move the needle tip and fixation member in an opposing direction 1002. Opposing direction 1002 is considered a retrograde direction.

Both needles 1030a, 1030b may be the same as each other, and operate, sequentially in the same or similar fashion. In general, both needles 1030a, 1030b include a hook portion 1032a, 1032b (shown in FIG. 10G) configured to engage a fixation member (5a, 5b, 905a, 905b). Both needles 1030a, 1030b may be formed of a spring steel or Nitinol and may be formed in a relaxed but curved configuration. Needles 1030a, 1030b may then be stressed to a straightened configuration while recessed with first jaw 1050 while placing the first jaw 1050 under the target leaflet. Advancing the needle 1030a, pushes needle 1030a out of a tip 1051 of jaw 1050, the needle returning to its curved relaxed configuration to curve and point the tip 1038 in a second direction 1002. FIG. 10F illustrates one of the needles 1030a or 1030b in its relaxed form. Needle is formed such that pushing a rod along shaft 1012 via an actuator on the handle, axially slides needle shaft portion 1031 in a distal direction 1001 and pushes needle tip in a proximal (retrograde) direction 1002.

As needle 1030a exits through aperture 1052a, hook portion 1032a may remove fixation member 5a 905a from cleat 1056a. Needle 1030a includes a tissue piercing tip 1038a configured to pierce through leaflet 10a. This forms a passage to push the fixation member 5a, 905a through the leaflet 10a and onto the external tissue surface 3. FIG. 10C illustrates another view of the system 1000, illustrating needle 1030a. Needle 1030a may extend through opening 1022. Opening 1022 is sufficiently large to allow passage of fixation member 5a 905a therethrough. Once the fixation member is though the leaflet and on the external surface 3, as illustrated in FIG. 1013, the second jaw 1020 may be axially retracted. While retracting, the opening 1022 slides over the fixation member 5a, 905a. Needle 1030a may also be retracted back into channel 1053a, leaving fixation member 5a, 905a on external surface of capsule leaflet 10a.

Once the first needle 1030a is retracted back into the first jaw 1050, instrument 1010 may be rotated or moved to place the first jaw 1050 under the second leaflet 10b. The instrument shaft 1012 may be rotated about 180 degrees to place the first jaw 1050 under the second leaflet 10b. Instrument 1010 preferably may not require withdrawal from the capsule area between passes through the two leaflets 10a, 10b. Instrument 1010 is shown with the first jaw 1050 under the second leaflet 10b in FIG. 10D. Once in position, similar to the first pass, a second needle 1030b may be advanced to first engage the second fixation member 5b, 905b and remove it from cleat 1056b. Tissue piercing tip 1038 of needle 1030b may then pierce leaflet 10b through to the external surface 3 and push fixation member 5b, 905b with it. This preferably places fixation member on external surface 3. Needle 1030b may then be retracted back through opening 1022 of second jaw 1020 and into first jaw 1050. With both fixation members placed on external surface, instrument 1010 may be removed from repair construct (800, 810, 820, 830, 840, 900) and may be removed from target area. Tension on suture limbs, away from the external surface, in a proximal direction 1002 may reduce the opening 20, deploy the fixation members and lock knot 909, as disclosed earlier. In other embodiments of system 1000, fixation members (5a, 5b, 905a, 905b) may be provided engaged with hook 1032 and housed within the corresponding channel 1053. This would eliminate the need for any cleats 1056.

Figure 12A:
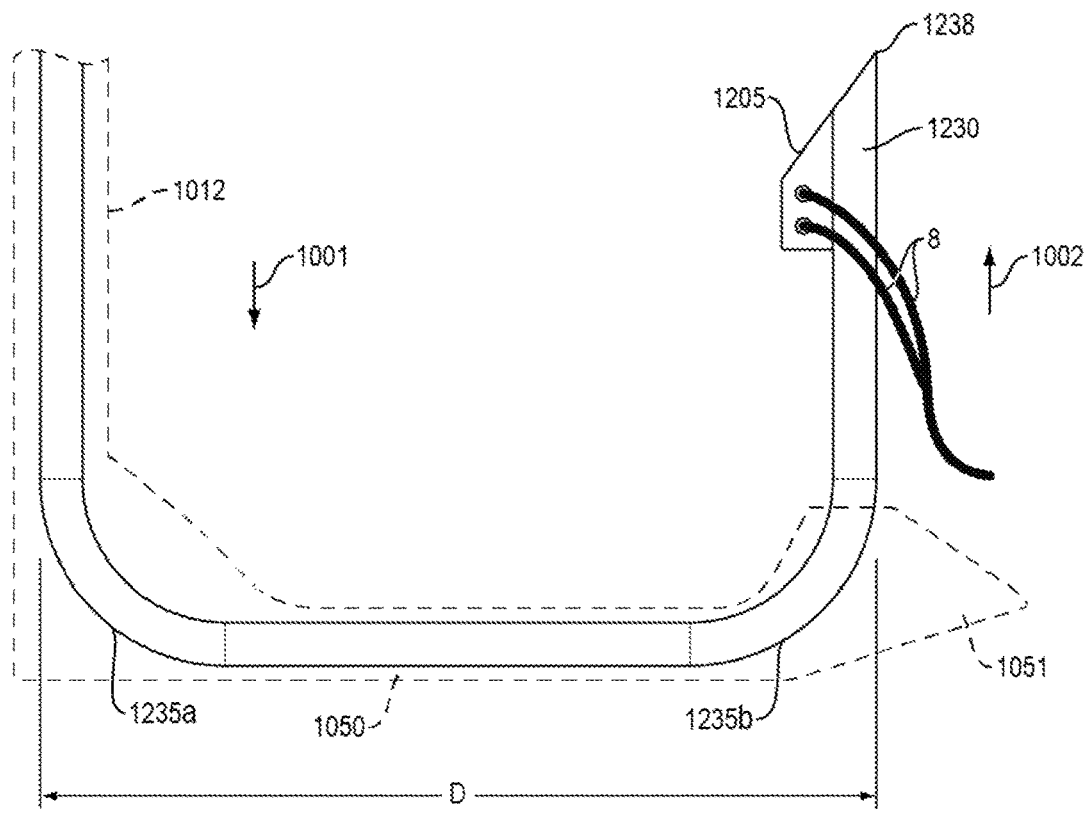
FIGS. 12A-12C illustrate a working end of a repair system including a slotted needle, in accordance with this disclosure.
Figure 12B:
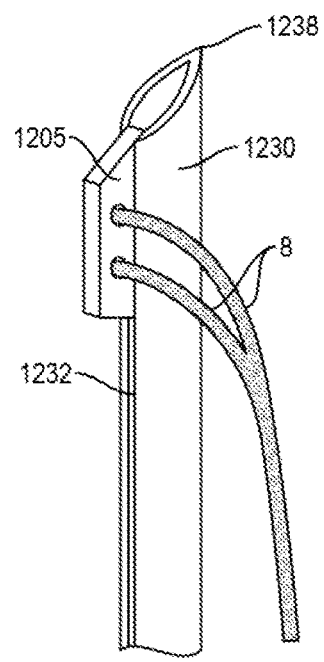
Figure 12C:
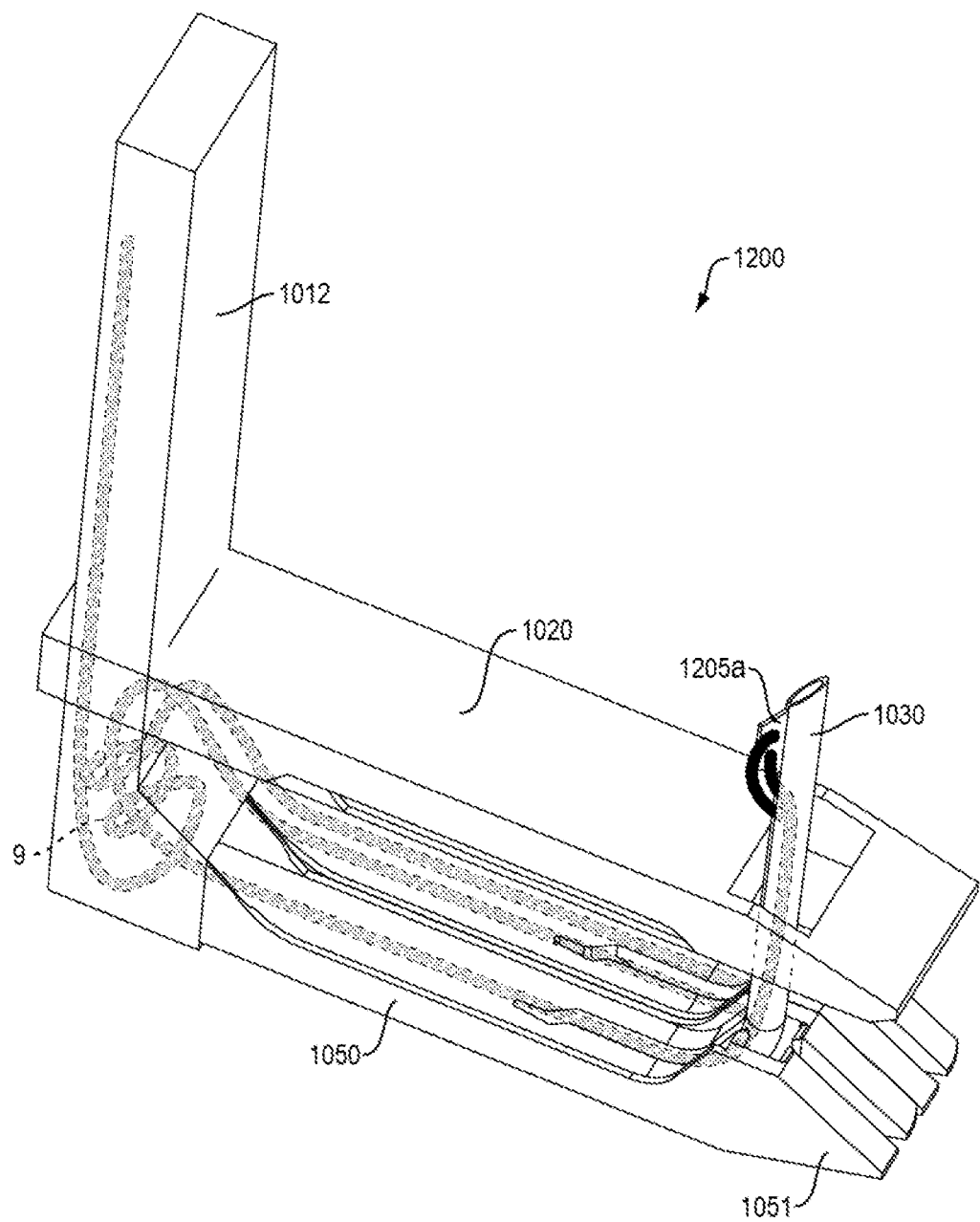

FIG. 12A-12C illustrate an alternative embodiment system 1200 and needle 1230, similar to system 1000. Like components are given the same numerical indicator. This embodiment may include a fixation member that is a rigid anchor 1205 slidingly coupled to a slotted 1232 in a needle 1230. Rigid anchor 1205 and slotted needle 1230 may be similar to the constructs disclosed in at least U.S. Pat. No. 7,153,312, commonly owned and herein incorporate by reference in its entirety. FIG. 12A illustrates the needle 1230 relative to the first jaw 1050 and shaft 1012 (shown as broken lines for reference). Similar to the needle 1030, needle 1230 may be formed of a spring steel or Nitinol and formed with bends therealong. Bends are formed to place the needle under the capsule leaflet 10a or 10b and along a preferred distance "D" before extending retrograde (1002) and through the corresponding capsule leaflet. Bends preferably have a tight radius as the available space under the capsule 10 is minimal. Needle 1230 preferably has two discrete bends 1235a, 1235b defining length "D" to minimize the distance the apparatus protrudes into the joint, however a single radius may also be utilized. Length D is at least 5 mm such that the needle tip 1238 pierces through the capsule leaflet at a location spaced away from the leaflet edge. This helps ensure that the leaflet can be pierced at a location spaced away from tissue opening 20, which may be uneven or jagged. At least the distal end of needle 1230 may be hollow and includes an elongate slot 1232, in which anchor 1205 may slide. Anchor 1205 may be operatively coupled to suture 8. Withdrawing needle 1230 once it has pierced the leaflet to place anchor therethrough, concomitantly removes anchor 1205 from the slot 1232. System 1200 may include two needles, 1230a and 1230b (1230b not shown) that extend along and out of first jaw 1050 in a similar manner to needles 1030*a*, 1030*b*. FIG. 12C illustrates system 1200 with a first of the two needles 1230*a* extended through the second jaw 1020. Like system 1000, opening 1022 is configured to allow passage of needle 1230 and rigid anchor 1205 therethrough. Suture 8 extends from a first anchor 1205*a*, along first jaw 1050. Suture routing may form a construct similar to suture path shown in FIG. 8E. Within shaft 1012, suture 8 may extend through knot 9, back through first jaw 1050 and then loops through a second anchor (not shown). Suture 8 then extends from second anchor and forms knot 9 before extending along shaft 1012.

Figure 14A:
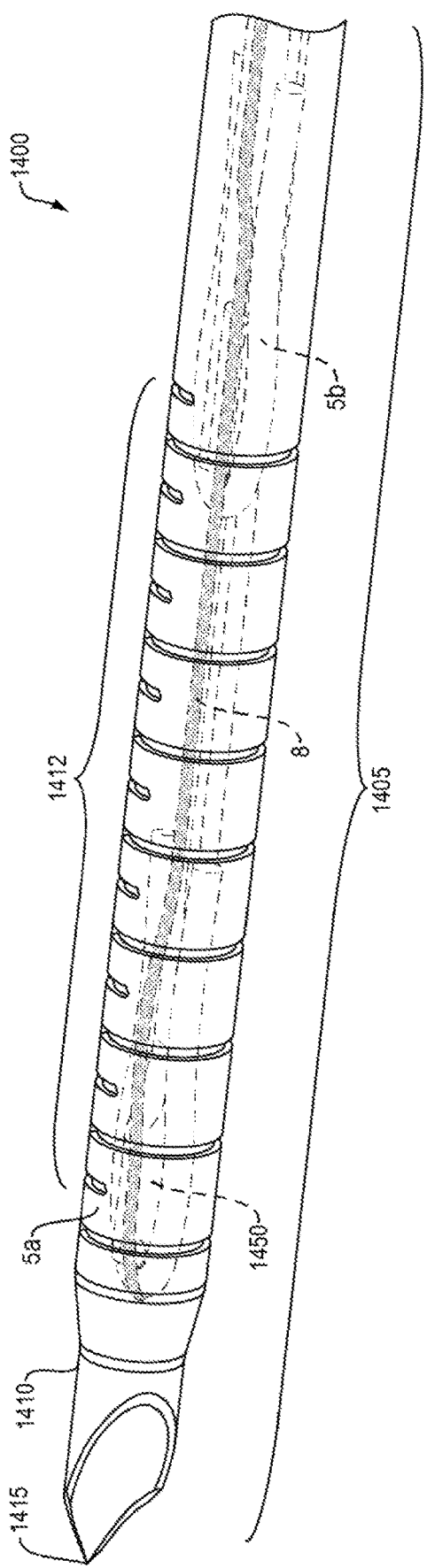
FIGS. 14A-14D illustrate various views and methods of use of an articulating repair system, in accordance with this disclosure.
Figure 14B:
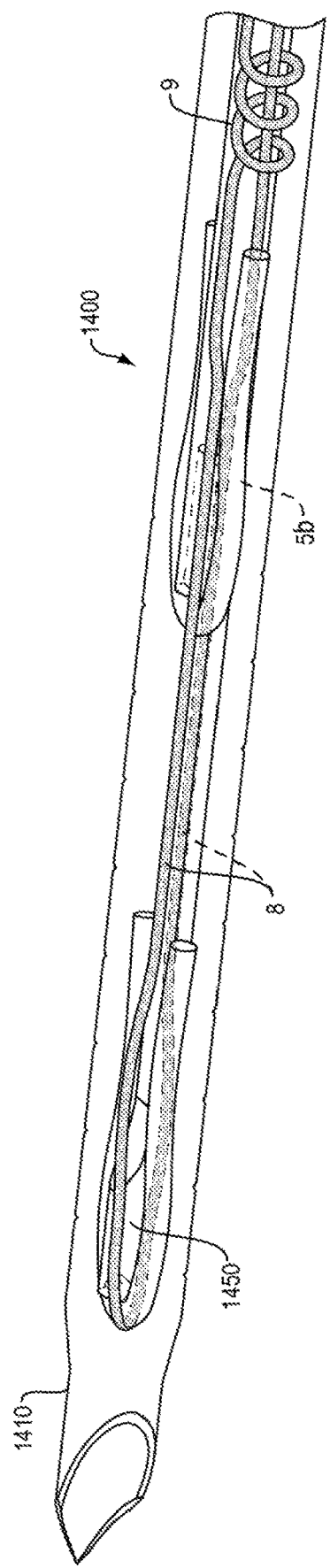

FIGS. 14A-14D illustrate another example embodiment of a system that may place fixation members on an external surface 3 of the capsule 10. System 1400 may close an opening 20 through the capsule 10 with a construct and method similar to that shown in FIG. 8A. FIG. 14A and FIG. 14B illustrates a distal end of instrument 1405 of the system 1400, the distal end 1405 defining a hollow needle 1410. FIG. 14B illustrates a simplified distal end 1405, with portions removed for simplification of understanding. Needle 1410 may be configured to articulate. Instrument 1405 may include an articulation control (not shown) operable by a user to selectively move an articulable portion 1412 between non-articulated and articulated configurations. The articulable portion 1412 may include a plurality of cutouts extending substantially in a transverse direction across a diameter of the needle 1410 and arranged along at least a portion of the length of the needle 1410 to provide a desired flexibility. Cutouts may be configured to articulate to a target bend radius, or a plurality of bend or curves. Known in the art, a pull shaft or rod (not shown) may be coupled to a distal end of the articulable portion 1412, such that actuation of the pull rod, via the articulation control may selectively move the articulable portion 1412 device between non-articulated and articulated configurations.

Figure 14C:
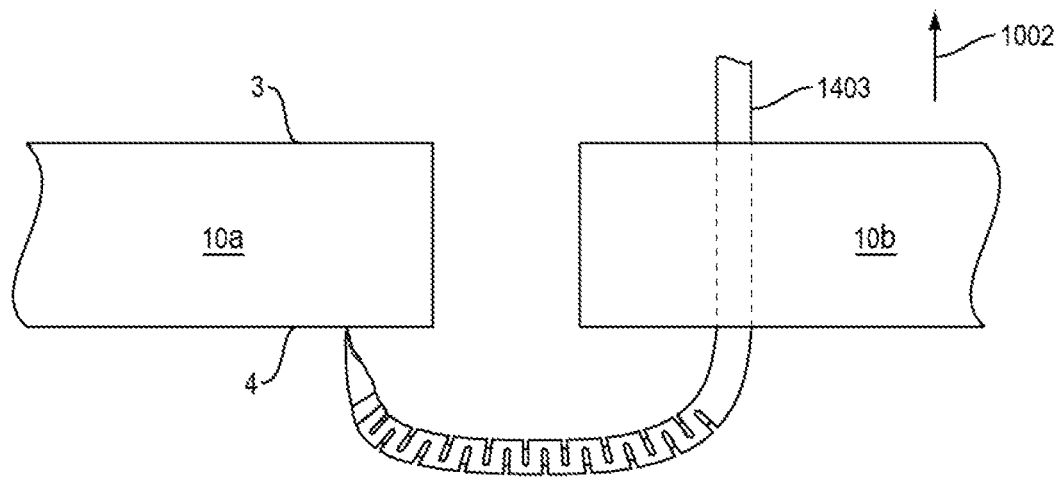
Figure 14D:
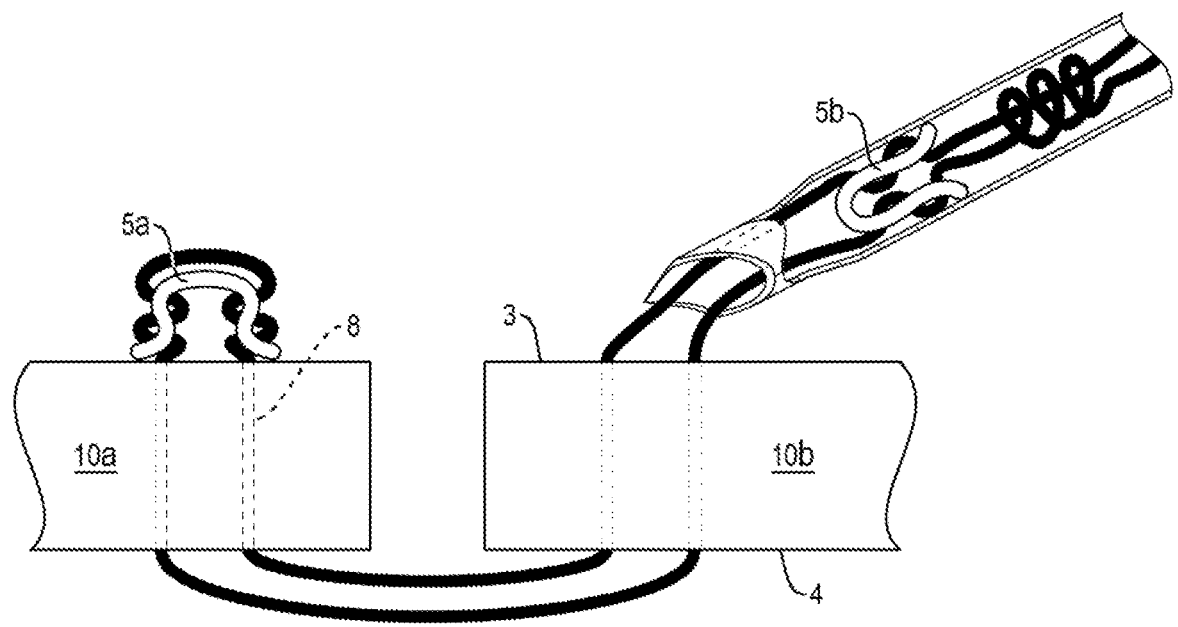

FIG. 14A-14B illustrates the distal end 1405 in a straight configuration. Needle distal tip 1415 is configured to pierce the capsule tissue 10. Needle 1410 is hollow and houses a repair construct therein, such as repair construct 800. Needle 1410 houses a first fixation member 5*a*, a second fixation member 5*b*, a flexible member 8 operatively coupled therebetween, with a preformed knot 9 formed by the flexible member. System 1400 may be placed through a second leaflet 10*b* in a straight configuration, or a less articulated configuration. Once through the second leaflet 10*b*, distal end 1405 may be articulated to place needle distal tip 1415 under a first leaflet 10*a*, as illustrated in FIG. 14C. During articulation, needle tip 1415 may be pushed, retrograde, through the first leaflet 10*a*. In other embodiments, instrument shaft 1403 may be retracted while in an articulated configuration to place tip 1415 through thickness of first leaflet 10*a* such that needle tip is at external surface 3. First fixation member 5*a* may then be pushed along and out of needle 1410 via a flexible push rod 1450 operatively coupled to an actuation lever of handle (not shown). Needle distal end may then be removed from first leaflet 10*a*, leaving first fixation member 5*a* on the external surface 3, as illustrated in FIG. 14D.

System 1400 may then be changed to a lesser articulated configuration and retracted to withdraw the tip 1415 through the second leaflet 10*b*. This places the suture 8 through the second leaflet 10*b*. With the entire instrument external to the capsule 10, as illustrated in FIG. 14D, the second fixation member 5*b* may then be pushed along out of needle 1410 via flexible push rod 1450 (illustrated in FIGS. 14A and 14B). A preformed knot 9 in the suture 8 may also be removed or operatively detached from instrument. Similar to methods disclosed earlier, tension on the suture limbs may close the opening 20, deploy the two fixation members 5*a*, 5*b* and may lock knot 9.

Figure 15A:
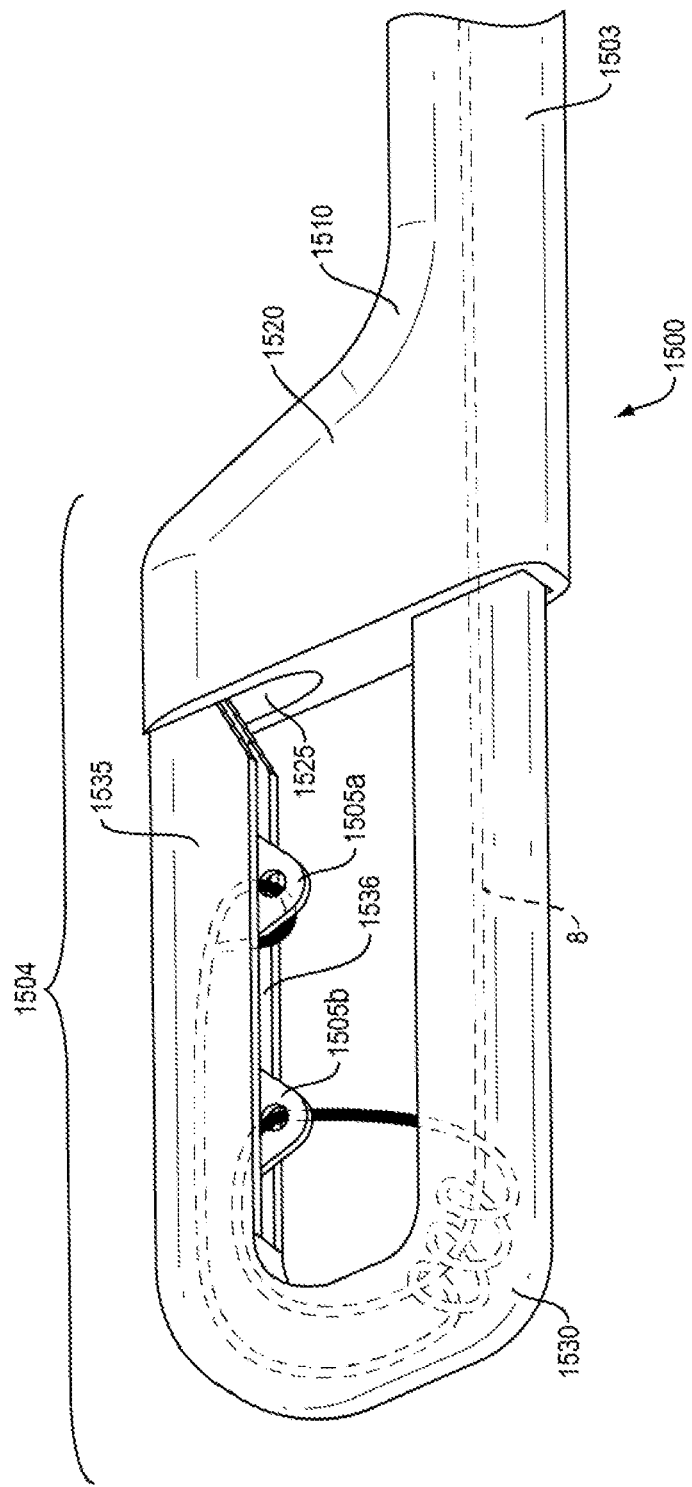
Figure 15B:
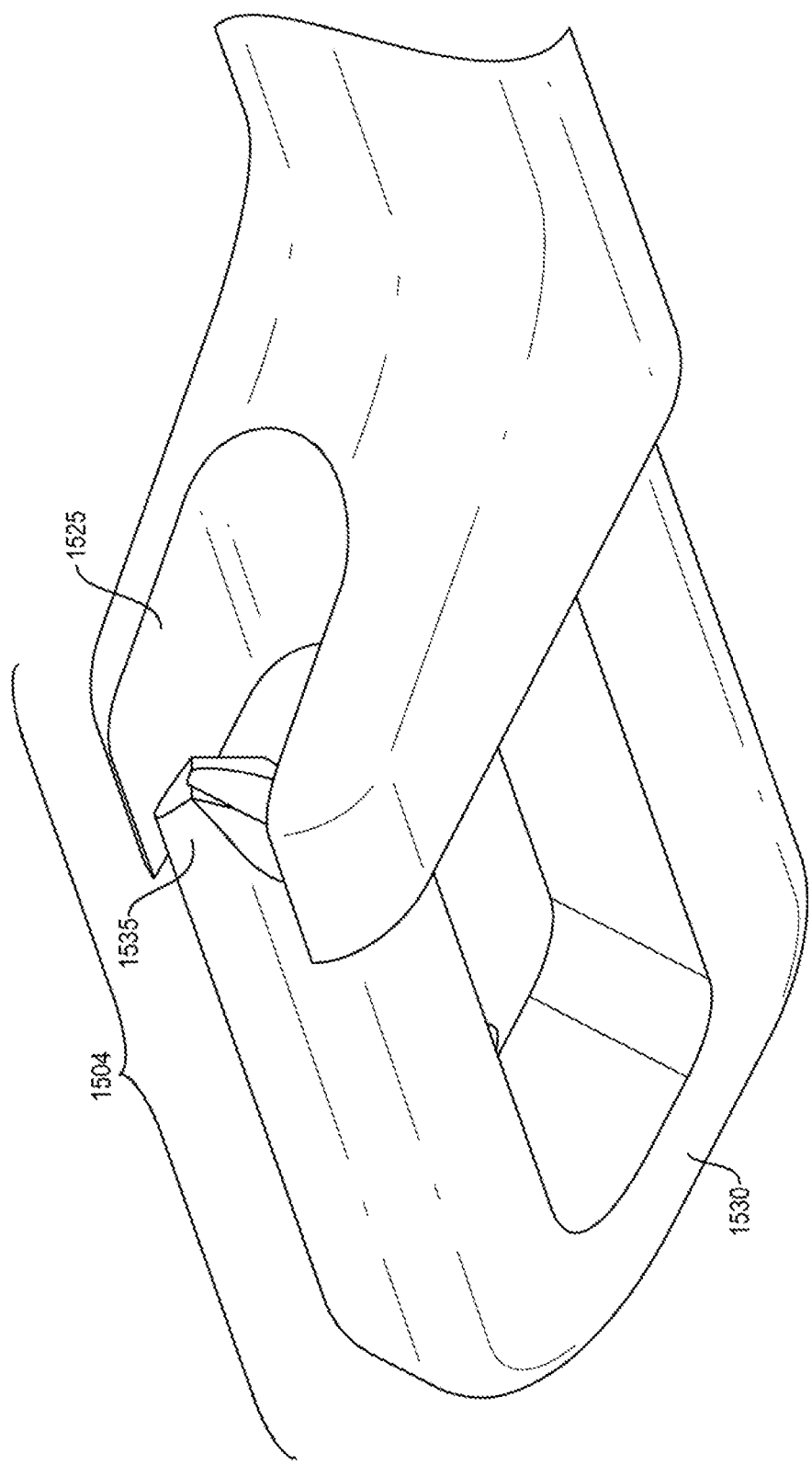

FIG. 15A-15H illustrate another example system 1500 that may place fixation members in a retrograde direction through a tissue and onto an external surface 3 of tissue. System 1500 includes instrument 1510 and repair construct that may be similar to construct 840. FIG. 15A illustrates a working end 1504 of instrument 1510 with construct 840 assembled thereto. Working end 1504 extends distally from a shaft 1503. A proximal end of shaft (not shown) may include a handle and actuation means to actuate various components of the working end 1504. Working end 104 may include an upper jaw 1520 with an axial channel 1525 therethrough. Axial channel 1525 may be laterally offset from a longitudinal axis of shaft. Working end 1504 may also include a lower jaw 1530. Lower jaw 1530 may extend from shaft distal end and may include two discrete bends. At least one of the upper jaw 1520 or lower jaw 1530 may slide along the longitudinal axis of shaft 103 to move the two jaws relative to each other. Lower jaw end defines a slotted needle 1535, with a tissue piercing tip. Slotted needle 1535 may move from a first open configuration, to a closed configuration. In an open configuration, tissue may be placed between the needle tip and upper jaw 1520. In the closed configuration, the needle tip may be disposed within channel 1525. Lower jaw 1530 may house or retain the repair construct, such as contract 800, 810, 820, 830 or 840. Slotted needle 1535 may house at least two fixation members 1505*a*, 1505*b* therein. Fixation members 1505*a*, 1505*b* may extend through slot 1536 and couple to suture 8. Suture 8 may be recessed within instrument 1510, as shown, or may extend along an external surface of the instrument 1510 in other embodiments.

Figure 15C:
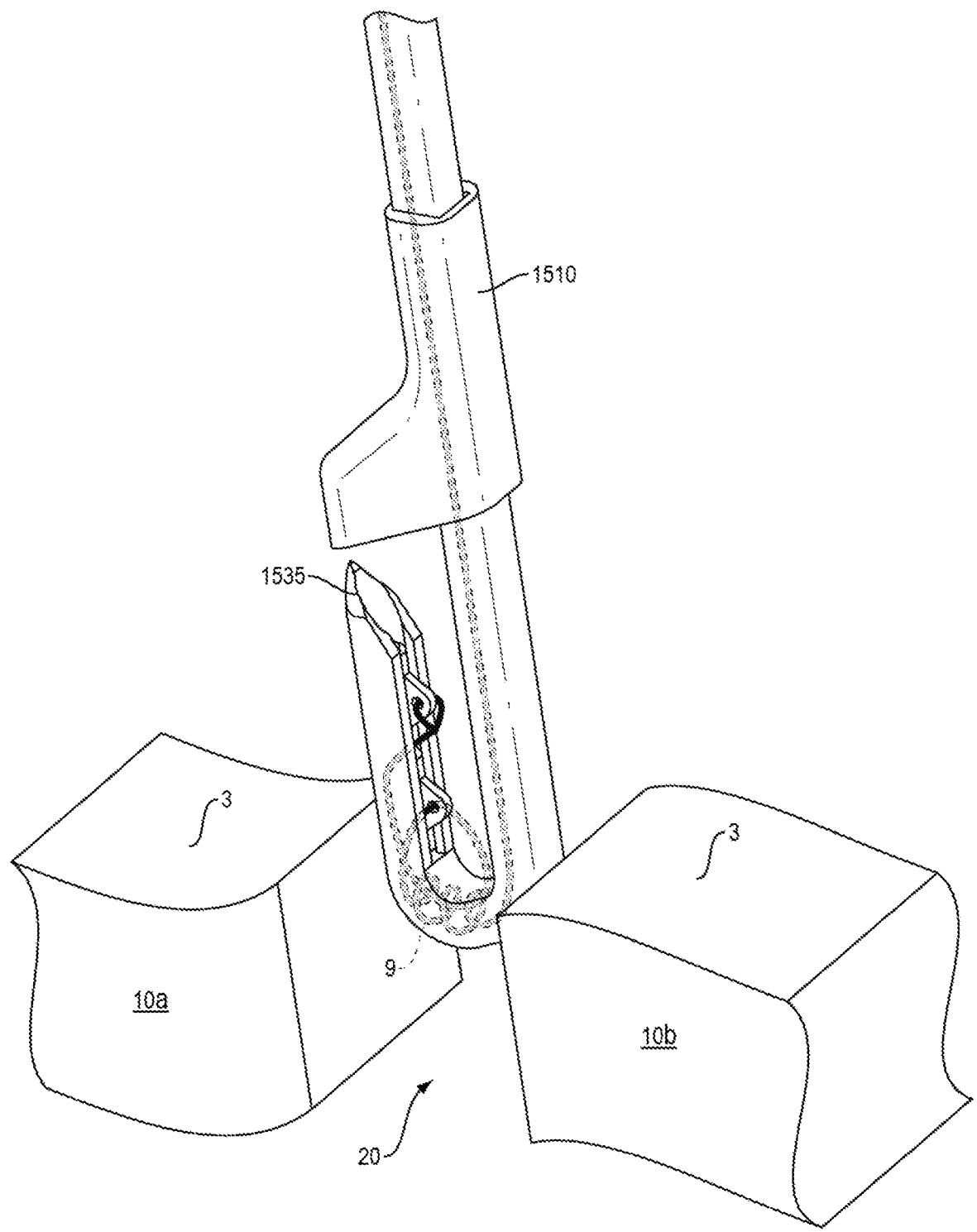
Figure 15D:
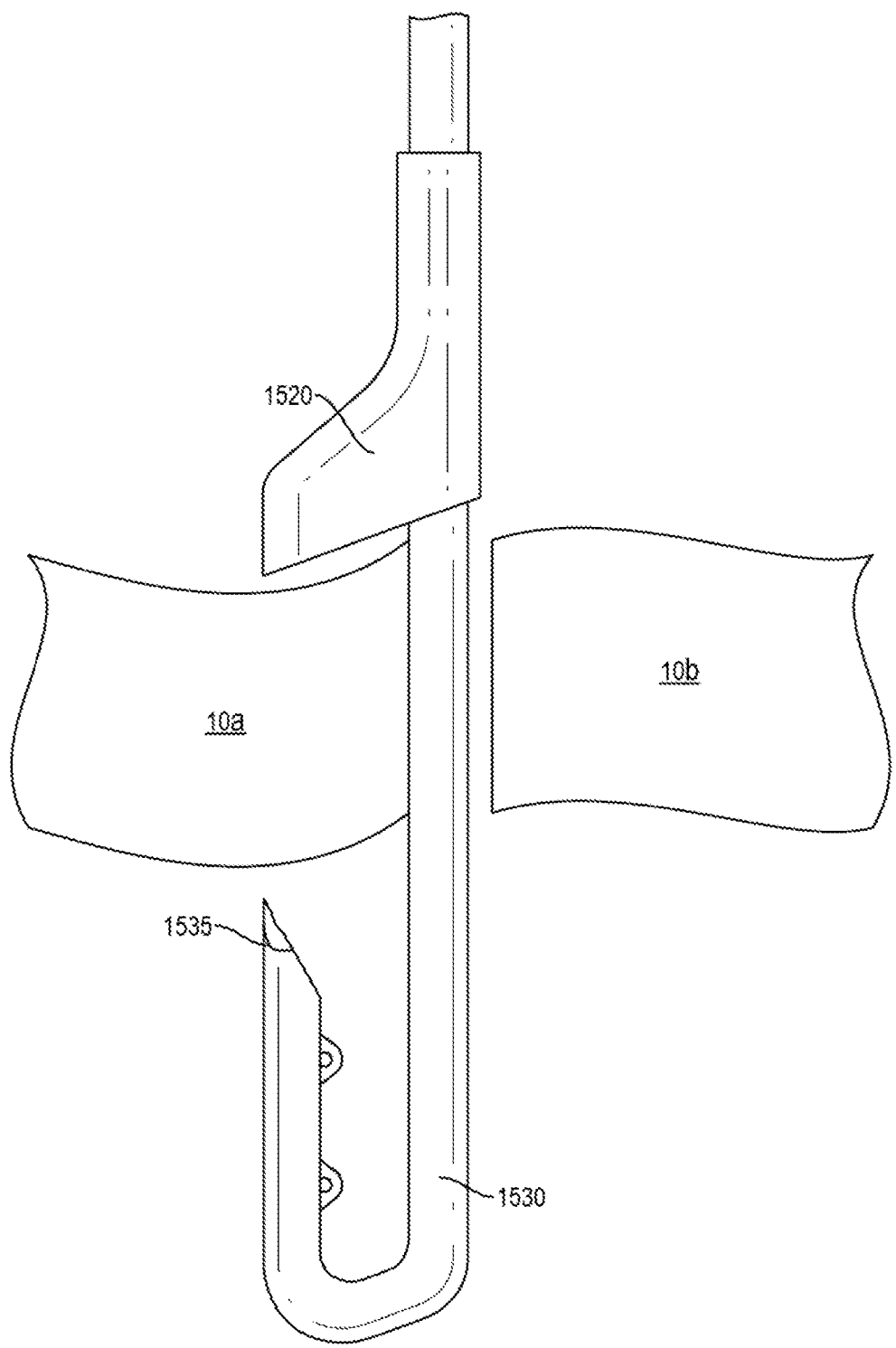
Figure 15G:
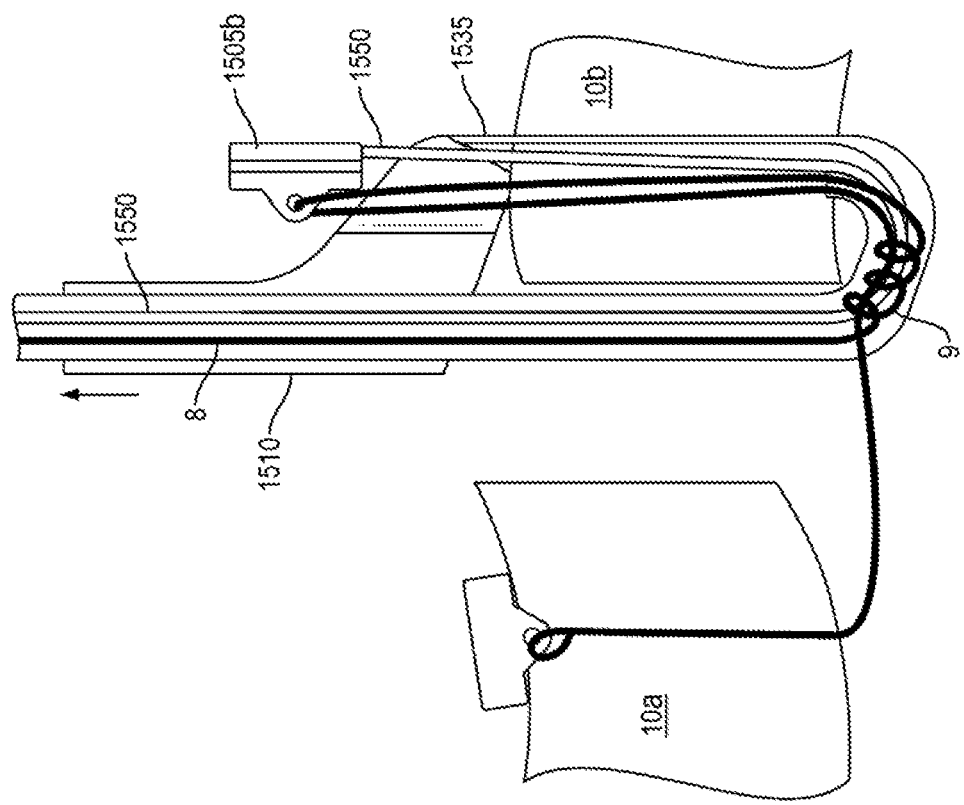
Figure 15H:
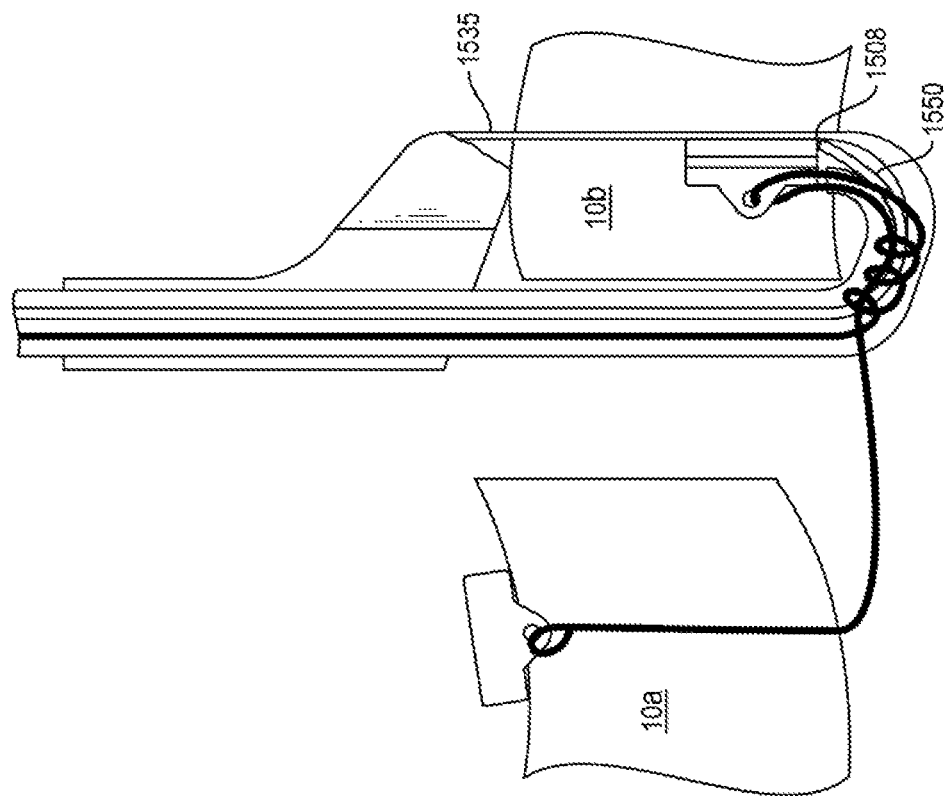

System 1500 is configured to be placed through opening 20 between leaflets 10*a*, 10*b*, as illustrated in FIG. 15C. System may then hook around first leaflet 10*a*, while in the open configuration as defined herein and illustrated in FIG. 15D. FIG. 15D illustrates the system without the suture 8 for simplicity of the figure. Lower jaw 1530 or upper jaw 1520 may slide axially to the closed configuration. This concomitantly pierces the first leaflet 10*a* and ensures the needle tip exits the leaflet 10*a* on the external side 3. A cross section of system 1500 is illustrated in FIG. 15E in the closed configuration with the needle tip adjacent the external surface 3 of leaflet 10*a*. FIG. 15E illustrates the two fixation members 1505*a*, 1505*b* with the suture removed for simplicity of understanding. Fixation members 1505*a* 1505*b* may be rigid members, and may include tabs 1506*a*, 1506*b* that extend through a slot 1536 of needle 1535. In other embodiments, fixation members may be entirely disposed within the slots 1536 and suture may wrap around the fixation members or extend through a through-hole through a body of the fixation member. Instrument 1510 includes a push rod 1550. Push rod 1550 is operatively coupled at a proximal end to an actuation means associated with the handle (not shown). Push rod 1550 is provided with a distal tip operatively coupled to the first fixation member 1505*a* and extending through a through-hole 1507 or channel of the second fixation. Axially advancing push rod 1550 advances the first fixation member in a retrograde direction 1002, through channel 1525 and adjacent external surface 3 of first leaflet 10*a*. FIG. 15F illustrates the first fixation device 1505*a* pushed through channel 1525. FIG. 15F is illustrated with the suture removed for simplicity of understanding. Push rod 1550 may then be retracted and instrument 1510 may be moved to the open configuration. In the open configuration, working end 1504 may then be removed from leaflet 10*a* and move to hook around the second leaflet 10*b*. FIG. 15G illustrates a cross section of the instrument 1510 around second leaflet 10*b*, and with the instrument in the closed configuration. Push rod 1550 may be withdraw from second fixation member through-hole 1507. Push rod 1550 may be sprung loaded, such that withdrawal places push rod distal end on a push surface 1508 of second fixation member 1505*b*. Axially advancing push rod 1550 axially advances second fixation member 1505*b*, in a retrograde direction. Second fixation member 1505*b* may be pushed through channel 1525 to be placed on external side or surface 3 of leaflet 10*b*, illustrated in FIG. 15H. Push rod may then be axially retracted, and instrument 1510 moved to open configuration. Tension in a retrograde direction 1002 on suture 8 may draw the opening 20 to a closed configuration, rotate or deploy the fixation members 1505*a*, 1505*b* and lock knot 9.

Those skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A method of repairing an opening through tissue, the opening disposed between a first leaflet and a second leaflet of tissue comprising:
    placing a distal end of a repair instrument along an internal surface of the first leaflet of tissue, a handle of the repair instrument disposed on an external side of the tissue, the repair instrument distal end housing a first fixation member coupled to a suture;
    actuating the repair instrument to pass the first fixation member and suture in a retrograde direction towards the handle, from the internal surface to an external surface of the first leaflet;
    deploying the first fixation member on the external surface, and once deployed,
        extending the suture through the second leaflet of tissue with the repair instrument;
        deploying a second fixation member coupled to the suture on an external surface of the second leaflet of tissue; and
        tensioning the suture to repair the opening through the tissue.

2. The method of claim 1 further comprising tensioning the suture to deploy the fixation members.

3. The method of claim 1 wherein placing the second fixation member comprise placing a distal end of the repair instrument along an internal surface of the second leaflet of tissue and passing the second fixation member in a retrograde direction through the second leaflet.

4. The method of claim 1 wherein tensioning the suture to repair the opening through the tissue comprises tightening a knot disposed on the internal surface while tensioning on suture limbs of the suture that extend from the external surface.

5. The method of claim 1 further comprising placing a proximal jaw of the repair instrument onto the first leaflet external surface before passing the first fixation member.

6. The method of claim 5 further comprising passing the first fixation member though an opening through the proximal jaw.

7. The method of claim 1 further comprising passing a piercing tip of the repair instrument in a retrograde direction before passing the first fixation member.

8. The method of claim 7 wherein passing the piercing tip includes sliding the piercing tip away from the repair instrument distal end.

9. The method of claim 1 wherein actuating the repair instrument slides a needle housed within the distal end, first towards the first fixation member to releasably engage the first fixation member, and then through the first leaflet.

10. The method of claim 9 wherein after the first fixation member has been passed through to the external surface, the needle is retracted back through the first leaflet.

11. The method of claim 1 wherein the first and second fixation member are all-suture anchors.

12. A method of repairing an opening through tissue, the opening disposed between a first leaflet and a second leaflet of tissue comprising:
    placing a distal end of a repair instrument along an internal surface of the first leaflet of tissue, the distal end housing a needle, a first fixation member and a suture, the needle slidably housed along the distal end and releasably coupled to the first fixation member, the suture fixedly coupled to the first fixation member, the placing with a handle of the repair instrument disposed on an external side of the tissue;
    engaging the repair instrument distal end with the internal surface of the first leaflet, and while engaged sliding the needle relative to the repair instrument distal end along the distal end and then through the first leaflet in a retrograde direction to pass the first fixation member and the suture in a retrograde direction towards the handle, from the internal surface to an external surface of the first leaflet;
    deploying the first fixation member on the external surface of the first leaflet, and once deployed;
        extending the suture through the second leaflet of tissue;
        placing a second fixation member coupled to the suture on an external surface of the second leaflet of tissue; and
        tensioning the suture to repair the opening through the tissue.

13. The method of claim 12 wherein the first and second fixation members are all-suture anchors.

14. The method of claim 12 wherein placing the second fixation member comprise placing a distal end of the repair instrument along an internal surface of the second leaflet of tissue and passing the second fixation member in a retrograde direction with the repair instrument through the second leaflet.

15. The method of claim 12 wherein tensioning the suture to repair the opening through the tissue comprises tightening a knot disposed on the internal surface while tensioning on suture limbs of the suture that extend from the external surface.

16. The method of claim 12 further comprising placing a proximal jaw of the repair instrument onto the first leaflet external surface before passing the first fixation member.

17. The method of claim 16 further comprising passing the first fixation member though an opening through the proximal jaw.

18. The method of claim 12 wherein the needle comprises a hook for releasably engaging the first fixation member.

19. A method of repairing an opening through tissue, the opening disposed between a first leaflet and a second leaflet of tissue comprising:

placing a distal jaw of a repair instrument through the opening and along an internal surface of the first leaflet of tissue, a handle of the repair instrument disposed on an external side of the tissue, the repair instrument distal jaw housing a first fixation member coupled to a suture;

placing a proximal jaw of the repair instrument along an external surface of the first leaflet of tissue, so as to stabilize the first leaflet between the distal and proximal jaw and while stabilized, actuating the repair instrument to pass the first fixation member and suture in a retrograde direction towards the proximal jaw, from the internal surface to the external surface of the first leaflet;

deploying the first fixation member on the external surface, and once deployed, extending the suture through the second leaflet of tissue with the repair instrument;

deploying a second fixation member coupled to the suture on an external surface of the second leaflet of tissue; and tensioning the suture to repair the opening through the tissue.

* * * * *